(12) United States Patent
Keenan et al.

(10) Patent No.: US 9,399,096 B2
(45) Date of Patent: Jul. 26, 2016

(54) AUTOMATIC CLOSED-LOOP CONTROL ADJUSTMENTS AND INFUSION SYSTEMS INCORPORATING SAME

(71) Applicant: MEDTRONIC MINIMED, INC., Northridge, CA (US)

(72) Inventors: Desmond Barry Keenan, Hollywood, CA (US); John J. Mastrototaro, Los Angeles, CA (US); Benyamin Grosman, North Hollywood, CA (US); Anirban Roy, Calabasas, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 93 days.

(21) Appl. No.: 14/174,501

(22) Filed: Feb. 6, 2014

(65) Prior Publication Data

US 2015/0217052 A1   Aug. 6, 2015

(51) Int. Cl.
*A61M 5/172*   (2006.01)
*A61M 5/145*   (2006.01)
*A61M 5/142*   (2006.01)

(52) U.S. Cl.
CPC ........... *A61M 5/1723* (2013.01); *A61M 5/1452* (2013.01); *A61M 5/14248* (2013.01); *A61M 2005/14208* (2013.01); *A61M 2205/18* (2013.01); *A61M 2205/3365* (2013.01);
(Continued)

(58) Field of Classification Search
CPC .................. A61M 5/1723; A61M 2005/1401; A61M 2205/3303; A61M 2205/502; A61M 2205/3584; A61M 2205/52; A61M 2205/3327; A61M 5/1452; A61M 5/14248; A61M 2205/18; A61M 2205/702; A61M 2205/3365; A61M 2205/3569; A61M 2205/3592; A61M 2205/70; A61M 2005/14208; A61M 2205/8212
USPC .................................................... 604/66, 504
See application file for complete search history.

(56) References Cited

U.S. PATENT DOCUMENTS 3,631,847 A   1/1972   Hobbs, II
4,212,738 A   7/1980   Henne
(Continued)

FOREIGN PATENT DOCUMENTS

DE   4329229   3/1995
EP   0319268   11/1988
(Continued)

OTHER PUBLICATIONS

PCT Search Report (PCT/US02/03299), Oct. 31, 2002, Medtronic Minimed, Inc.
(Continued)

*Primary Examiner* — Kevin C Sirmons
*Assistant Examiner* — Amber Stiles
(74) *Attorney, Agent, or Firm* — Ingrassia Fisher & Lorenz, P.C.

(57) ABSTRACT

Infusion systems, infusion devices, and related operating methods are provided. An exemplary method of operating an infusion device capable of delivering fluid to a user involves identifying a condition of the user that is likely to influence a response to the fluid in the body of the user and classifying the condition as a first type of a plurality of types of conditions. After classifying the condition as the first type, the method continues by adjusting control information for operating the infusion device based on the first type and operating the infusion device to deliver the fluid to the user in accordance with the adjusted control information.

15 Claims, 10 Drawing Sheets

(52) U.S. Cl.
CPC .......... A61M2205/3569 (2013.01); A61M 2205/3592 (2013.01); A61M 2205/70 (2013.01); A61M 2205/702 (2013.01); A61M 2205/8212 (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |

(56) References Cited

U.S. PATENT DOCUMENTS

| | | | |
|---|---|---|---|
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,589,229 B1 | 7/2003 | Connelly et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,740,072 B2 | 5/2004 | Starkweather et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,827,702 B2 | 12/2004 | Lebel et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Vasko | |
| 7,323,142 B2 | 1/2008 | Pendo et al. | |
| 7,396,330 B2 | 7/2008 | Banet et al. | |
| 7,402,153 B2 | 7/2008 | Steil et al. | |
| 7,621,893 B2 | 11/2009 | Moberg et al. | |
| 8,603,026 B2 | 12/2013 | Favreau | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093034 A1* | 5/2004 | Girouard | A61M 5/1723 607/3 |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0220517 A1* | 11/2004 | Starkweather | A61M 5/172 604/67 |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2009/0069787 A1* | 3/2009 | Estes | A61M 5/1413 604/503 |
| 2009/0081951 A1 | 3/2009 | Erdmann et al. | |
| 2009/0082635 A1 | 3/2009 | Baldus et al. | |
| 2010/0145262 A1* | 6/2010 | Bengtsson | A61B 5/14532 604/66 |
| 2011/0233393 A1 | 9/2011 | Hanson et al. | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII]

(56) References Cited

OTHER PUBLICATIONS

With External Devices: Current Status. Update in Drug Delivery Systems, Chapter 13, pp. 163-183. Futura Publishing Company.
Skyler J Set al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual.
Disetronic H-TRON® plus Quick Start Manual.
Disetronic My Choice H-TRONplus Insulin Pump Reference Manual.
Disetronic H-TRON®plus Reference Manual.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.

Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference ofteh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompat-

(56) References Cited

OTHER PUBLICATIONS ible membrane, 2-methacryloyloxyethylphosphorylcholine -co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting Esao, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

Benyamin Grosman, Generation and Application of an insulin Limit for a Closed-Loop Operating Mode of an Insulin Infusion System, Filed Aug. 13, 2013, U.S. Appl. No. 13/966,120, United States Patent and Trademark Office.

\* cited by examiner

US 9,399,096 B2

AUTOMATIC CLOSED-LOOP CONTROL ADJUSTMENTS AND INFUSION SYSTEMS INCORPORATING SAME

TECHNICAL FIELD

Embodiments of the subject matter described herein relate generally to medical devices, and more particularly, embodiments of the subject matter relate to adjusting information used in providing closed-loop control of a fluid infusion device to account for events that affect a user's sensitivity to the fluid being administered.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Furthermore, a user's daily activities and experiences may cause that user's insulin response to vary throughout the course of a day or from one day to the next. Thus, it is desirable to account for the anticipated variations or fluctuations in the user's insulin response caused by the particular condition(s) experienced by the user. However, detecting the particular type of condition that the user is or has been experiencing is complicated by the fact that conditions having opposite effects on the user's insulin response could present themselves in the same way. For example, two different conditions experienced by the user could result in the same heart rate being exhibited by the user, but have opposite effects on the user's insulin response.

BRIEF SUMMARY

An embodiment of a method of operating an infusion device capable of delivering fluid to a user is provided. An exemplary method involves identifying a condition of the user that is likely to influence a response to the fluid in the body of the user and classifying the condition as a first type of a plurality of types of possible conditions in the body of the user. After classifying the condition, the method continues by adjusting control information for operating the infusion device based on the classified first type and operating the infusion device to deliver the fluid to the user in accordance with the adjusted control information.

In one embodiment, an infusion system is provided that includes a motor operable to deliver fluid to a user that is capable of influencing a first condition of the user, a sensing arrangement to obtain a measured value indicative of the first condition of the user, and a control system coupled to the motor and the sensing arrangement. The control system is configured to identify a second condition of the user that is likely to influence a response to the fluid in a body of the user, classify the second condition as a first type of a plurality of types of conditions, and after classifying the second condition as the first type, adjust control information for operating the motor based on the first type and operate the motor to deliver the fluid to the user based at least in part on the adjusted control information and a difference between a target value for the first condition of the user and the measured value.

In another embodiment, a method of operating an infusion device capable of delivering insulin to a user involves obtaining heart rate measurement data for the user, identifying an insulin sensitivity condition based on the heart rate measurement data, obtaining an activity metric for the user, and classifying the insulin sensitivity condition as a first type of a plurality of types of insulin sensitivity conditions based on the activity metric. After classifying the condition as the first type, the method continues by automatically adjusting control information for operating the infusion device based on the first type, determining delivery commands for operating a motor of the infusion device in accordance with the adjusted control information, and operating the motor to deliver the insulin to the user in accordance with the delivery commands.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
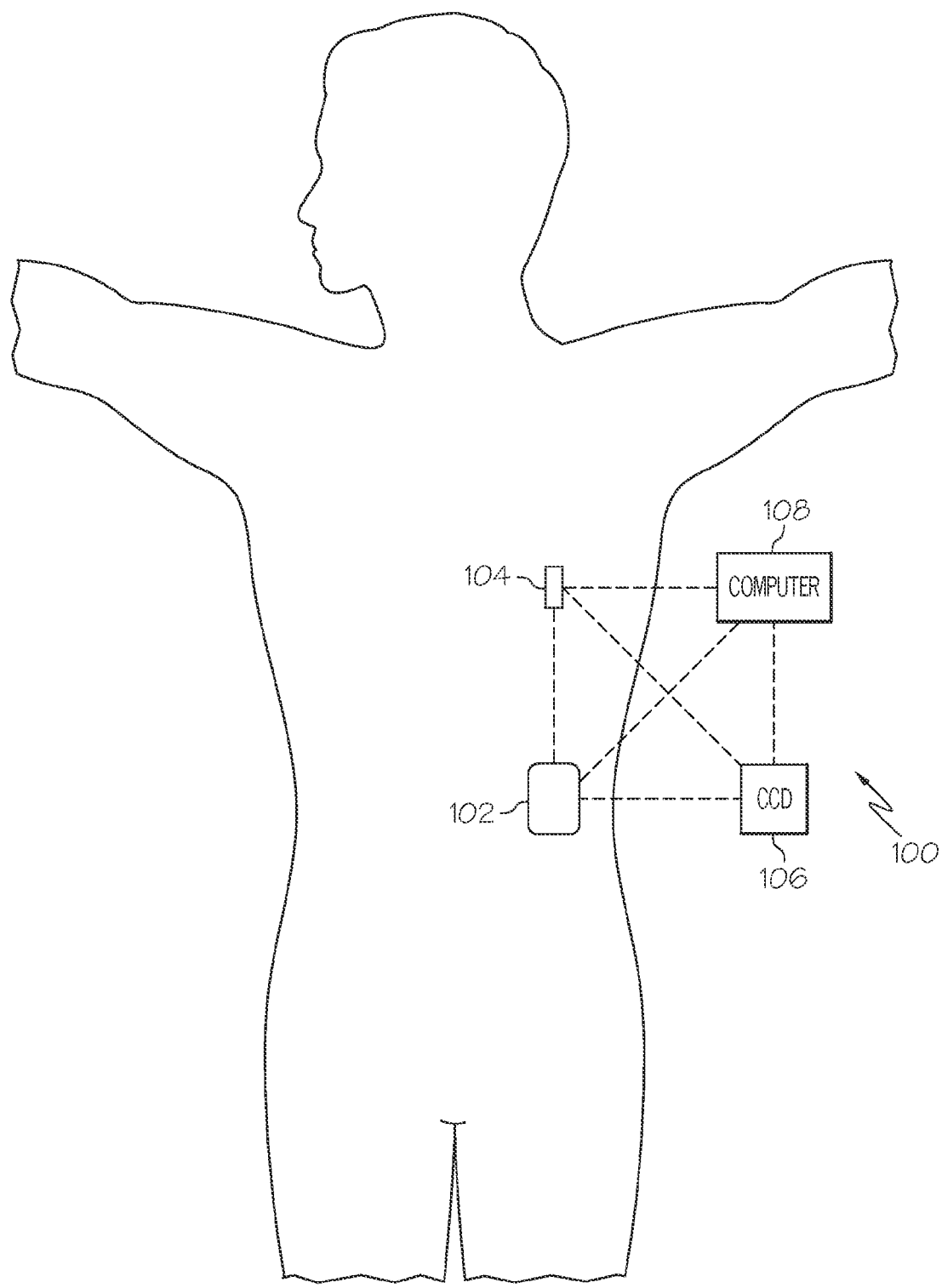
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. Delivery commands (or dosage commands) that govern operation of the motor are determined based on a difference between a measured value for a condition in the body of the user and a target value using closed-loop control to regulate the measured value to the target value. As described in greater detail below in the context of FIGS. 7-10, another condition of the user that is likely to influence the user's response (or sensitivity) to the fluid being administered is detected and identified or otherwise classified as a particular type of condition from among plurality of types of conditions that could influence the user's response to the fluid. Thereafter, at least some of the control information utilized by the closed-loop control to generate delivery commands and operate the infusion device are automatically adjusted based on that particular type of condition to account for the anticipated change in the user's response to the fluid. As a result, the closed-loop control utilizes the adjusted control information to generate delivery commands and operate the infusion device in accordance with the adjusted control information.

In exemplary embodiments, delivery commands for operating an insulin infusion device are determined based on a difference between a measured blood glucose value from the body of the user and a target blood glucose value by applying proportional-integral-derivative (PID) closed-loop control to regulate the measured value to the target value. In this regard, the proportional, integral, and derivative gain coefficients are respectively applied to the difference before performing the respective integral and derivative operations and combining the proportional, integral, and derivative components to arrive at a delivery command for operating a motor to deliver insulin to the body of the user. Heart rate measurement data for the user is obtained, and based on the heart rate measurement data, a condition of the user that is likely to influence the user's insulin response (or insulin sensitivity) is detected. An activity metric associated with the body of the user is calculated, determined, or otherwise obtained (e.g., using acceleration measurement data from an acceleration sensing arrangement) and utilized to classify the detected condition as being exercise or stress.

In response to detecting and identifying exercise, one or more of the PID gain coefficients are automatically decreased to account for an anticipated increase in the user's insulin sensitivity (e.g., a faster insulin response). In some embodiments, amount of the decrease may be based at least in part on the duration and/or the intensity of the exercise. Conversely, in response to detecting and identifying stress, one or more of the PID gain coefficients may be automatically increased to account for an anticipated increase in the user's insulin resistance (e.g., a slower insulin response). Similarly, the amount of the increase may be based at least in part on the duration and/or the intensity of the stress. Thereafter, the one or more adjusted PID gain coefficients are applied to subsequent differences between measured blood glucose values from the body of the user and the target blood glucose value to regulate the user's blood glucose in accordance with the adjusted PID gain coefficient(s).

In various embodiments, in addition or in alternative to adjusting one or more PID gain coefficients, one or more additional control parameters or other control information utilized to implement the closed-loop control may also be automatically adjusted to account for the detected exercise or stress. For example, one or more limits on the insulin infusion utilized by the closed-loop control as a safeguard when generating the delivery commands may automatically be adjusted to account for the anticipated change in the user's insulin response. In the case of exercise or another condition where the user's insulin sensitivity increases (or insulin response time decreases), an upper limit on the insulin infusion rate may be automatically reduced or decreased to prevent inadvertent overdelivery. Similarly, in the case of stress or another condition where the user's insulin resistance increases (or insulin response time increases), an upper limit on the insulin infusion rate may be automatically increased to account for the increased insulin resistance. Furthermore, in some embodiments, a target glucose setpoint value used by the PID control may also be adjusted (e.g., increased in the case of exercise or decreased in the case of stress) from its normal (or unadjusted) value to account for changes in the user's insulin response in addition to or in lieu of adjusting the PID gain coefficient(s). Various other control information or control parameters utilized for providing closed-loop control (e.g., one or more time limit(s), glucose setpoint(s), or the like) may also be adjusted to best account for the anticipated effect of the detected exercise or stress on the user throughout the duration of time during which closed-loop control is being provided.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or U.S. patent application Ser. No. 13/966,120, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
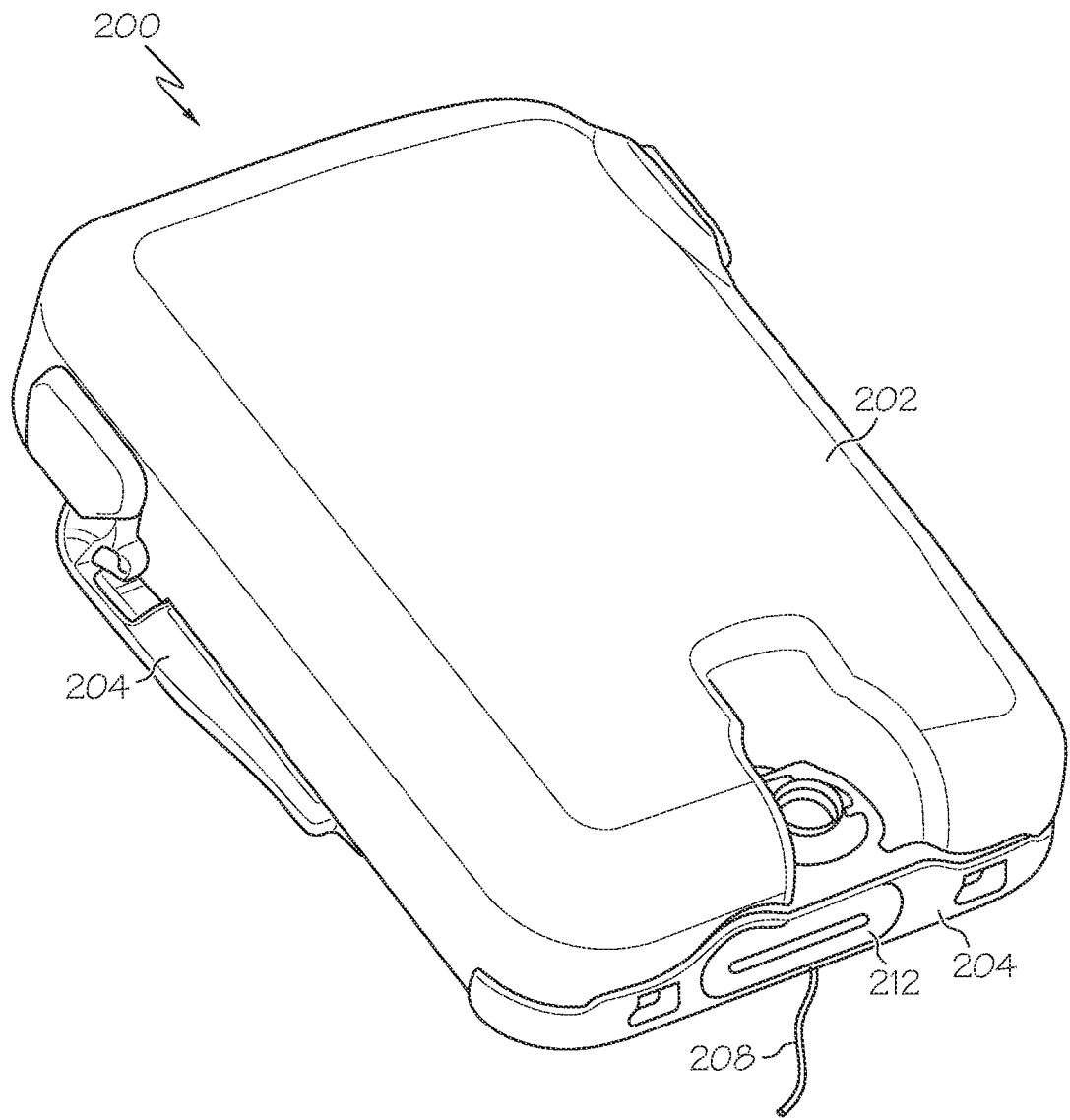
FIG. 2 is a perspective view of an exemplary embodiment of a fluid infusion device suitable for use in the infusion system of FIG. 1.
Figure 3:
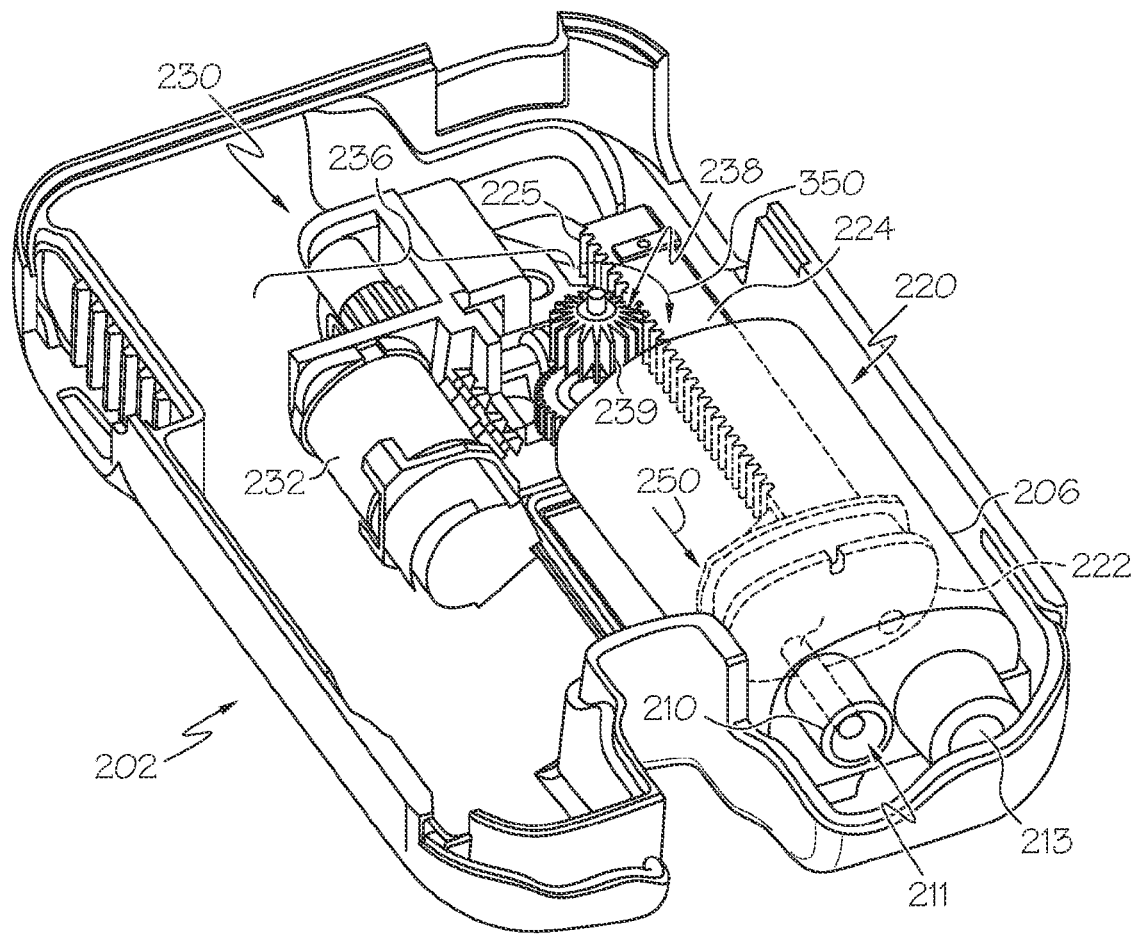
FIG. 3 is a perspective view that depicts the internal structure of the durable housing of the fluid infusion device shown in FIG. 2.

FIGS. 2-3 depict an exemplary embodiment of a fluid infusion device 200 suitable for use as the infusion device 102 in the infusion system 100 of FIG. 1. FIGS. 2-3 depict perspective views of the fluid infusion device 200, which includes a durable housing 202 and a base plate 204. While FIG. 2 depicts the durable housing 202 and the base plate 204 as being coupled together, in practice, the durable housing 202 and/or the base plate 204 may include features, structures, or elements to facilitate removable coupling (e.g., pawls, latches, rails, slots, keyways, buttons, or the like) and accommodate a removable/replaceable fluid reservoir 206. As illustrated in FIG. 3, in exemplary embodiments, the fluid reservoir 206 mates with, and is received by, the durable housing 202. In alternate embodiments, the fluid reservoir 206 mates with, and is received by, the base plate 204.

In exemplary embodiments, the base plate 204 is temporarily adhered to the skin of the user, as illustrated in FIG. 1 using, for example, an adhesive layer of material. After the base plate 204 is affixed to the skin of the user, a suitably configured insertion device or apparatus may be used to insert a fluid delivery needle or cannula 208 into the body of the user. The cannula 208 functions as one part of the fluid delivery path associated with the fluid infusion device 200. The durable housing 202 receives the fluid reservoir 206 and retains the fluid reservoir 206 in a substantially fixed position and orientation with respect to the durable housing 202 and the base place 204 while the durable housing 202 and the base plate 204 are coupled. The durable housing 202 is configured to secure to the base plate 204 in a specified orientation to engage the fluid reservoir 206 with a reservoir port receptacle formed in the durable housing 202. In particular embodiments, the fluid infusion device 200 includes certain features to orient, align, and position the durable housing 202 relative to the base plate 204 such that when the two components are coupled together, the fluid reservoir 206 is urged into the reservoir port receptacle to engage a sealing assembly and establish a fluid seal.

In exemplary embodiments, the fluid reservoir 206 includes a fluid delivery port 210 that cooperates with the reservoir port receptacle to establish a fluid delivery path. In this regard, the fluid delivery port 210 has an interior 211 defined therein that is shaped, sized, and otherwise configured to receive a sealing element when the fluid reservoir 206 is engaged with the reservoir port receptacle on base plate 204. The sealing element forms part of a sealing assembly for the fluid infusion device 200 and preferably includes one or more sealing elements and/or fluid delivery needles configured to establish fluid communication from the interior of the reservoir 206 to the cannula 208 via the fluid delivery port 210 and a mounting cap 212, and thereby establish a fluid delivery path from the reservoir 206 to the user via the cannula 208. In the illustrated embodiment, the fluid reservoir 206 includes a second fluid port for receiving fluid. For example, the second fluid port 213 may include a pierceable septum, a vented opening, or the like to accommodate filling (or refilling) of the fluid reservoir 206 by the patient, a doctor, a caregiver, or the like.

As illustrated in FIG. 3, the reservoir 206 includes a barrel 220 for containing fluid and a plunger 222 (or stopper) positioned to push fluid from inside the barrel 220 of the reservoir 206 along the fluid path through the cannula 208 to the user. A shaft 224 is mechanically coupled to or otherwise engages the plunger 222, and the shaft 224 has exposed teeth 225 that are configured to mechanically couple or otherwise engage the shaft 224 with a gear 238 of a drive system 230 contained in the durable housing 202. In this regard, the shaft 224 functions as a rack gear as part of a rack and pinion gear configuration. Although the subject matter may be described herein in the context of the shaft 224 being integral with or otherwise part of the plunger 222, in practice, the shaft 224 and the plunger 222 may be provided separately.

Various aspects of the motor drive system 230 may be similar to those described in U.S. patent application Ser. No. 13/049,803. The drive system 230 includes a motor 232 having a rotor that is mechanically coupled to a gear assembly 236 that translates rotation of the rotor to translational displacement the plunger 222 in the direction 250 of the fluid delivery port 210 to deliver fluid from the reservoir 206 to a user. Accordingly, the direction 250 may alternatively be referred to herein as the fluid delivery direction 250.

In exemplary embodiments, the motor 232 is realized as a DC motor, such as a stepper motor or brushless DC motor capable of precisely controlling the amount of displacement of the plunger 222 during operation of the infusion device 200. In exemplary embodiments, the rotor of the motor 232 is mechanically coupled to a rotary shaft, which, in turn, is mechanically coupled to a first gear of the gear assembly 236. For example, the first gear may be coaxial and/or concentric to and disposed about the rotary shaft, where the first gear is affixed to or otherwise integrated with the rotary shaft such that the first gear and the rotary shaft rotate in unison. The gear assembly 236 also includes a pinion gear 238 having exposed teeth 239 that are configured to mate with or otherwise engage the exposed teeth 225 on the shaft 224 when the reservoir 206 is seated in the durable housing 202, such that rotation or displacement of the pinion gear 238 in rotational delivery direction 350 produces a corresponding translational displacement of the shaft 224 and/or plunger 222 in the fluid delivery direction 250 to deliver fluid to the user.

During operation of the fluid infusion device 200, when the motor 232 is operated to rotate the rotor, the rotary shaft rotates in unison with the rotor to cause a corresponding rotation of the first gear, which, in turn, actuates the gears of the gear assembly 236 to produce a corresponding rotation or displacement of the pinion gear 238, which, in turn, displaces the shaft 224. In this manner, the rotary shaft translates rotation (or displacement) of the rotor into a corresponding rotation (or displacement) of the gear assembly 236 such that the teeth 239 of the pinion gear 238 apply force to the teeth 225 of the shaft 224 of the plunger 222 in the fluid delivery direction 250 to thereby displace the plunger 222 in the fluid delivery direction 250 and dispense, expel, or otherwise deliver fluid from the barrel 220 of the reservoir 206 to the user via the fluid delivery path provided by the cannula 208.

As described in greater detail below in the context of FIG. 7, in one or more exemplary embodiments, a motor position sensor (or rotor position sensor) is configured to measure, sense, or otherwise detect rotation (or displacement) of the rotary shaft and/or the rotor of the motor 232. The motor position sensor may be utilized to provide closed-loop control of the motor 232, such as, for example, as described in U.S. patent application Ser. No. 13/425,174, the subject matter of which is hereby incorporated by reference in its entirety. In exemplary embodiments, the rotary shaft includes, is coupled to, or is otherwise associated with a detectable feature that is measurable or otherwise detectable by the motor position sensor. In this regard, the detectable feature may rotate in unison with the rotary shaft. In one or more embodiments, the motor position sensor is realized as an incremental position sensor configured to measure, sense, or otherwise detect incremental rotations of the rotary shaft and/or the rotor of the motor 232. For example, in accordance with one or more embodiments, the motor position sensor is realized as a rotary encoder.

Figure 4:
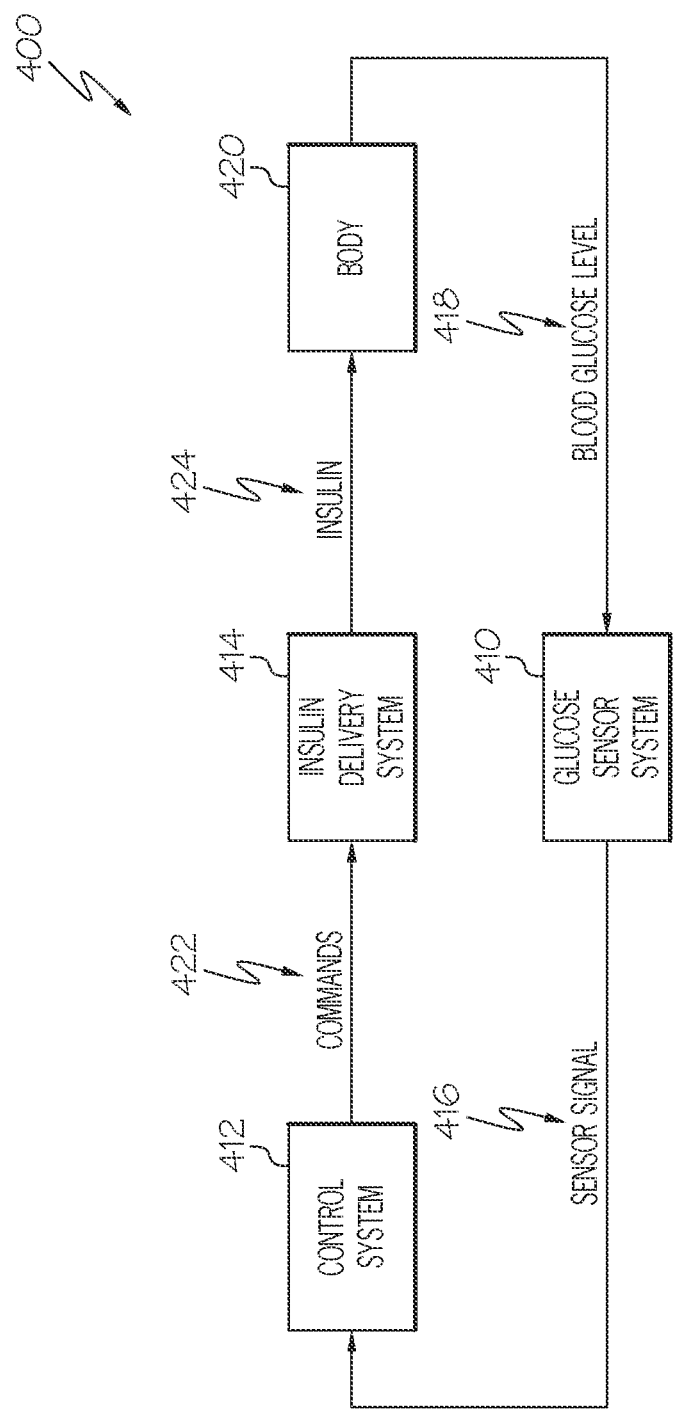
FIG. 4 is a block diagram of a closed-loop infusion system suitable for use with the infusion system of FIG. 1.

FIG. 4 depicts an exemplary embodiment of a closed-loop infusion system 400 suitable for use with or implementation by the infusion system 100 for regulating the rate of fluid infusion into a body of a user (e.g., by infusion device 102) based on feedback from an analyte concentration measurement taken from the body (e.g., via sensing arrangement 104). In exemplary embodiments, the infusion system 400 regulates the rate of insulin infusion into the body of a user based on a glucose concentration measurement taken from the body. In preferred embodiments, the infusion system 400 is designed to model a pancreatic beta cell ($\beta$-cell). In other words, the system controls the infusion device 102 to release insulin into a body of a user in a similar concentration profile as would be created by fully functioning human $\beta$-cells when responding to changes in blood glucose concentrations in the body. Thus, the infusion system 400 simulates the body's natural insulin response to blood glucose levels and not only makes efficient use of insulin, but also accounts for other bodily functions as well since insulin has both metabolic and mitogenic effects. However, the algorithms must model the $\beta$-cells closely, since algorithms that are designed to minimize glucose excursions in the body, without regard for how much insulin is delivered, may cause excessive weight gain, hypertension, and atherosclerosis. Thus, in some embodiments, the infusion system 400 is intended to emulate the in vivo insulin secretion pattern and to adjust this pattern consistent with the in vivo β-cell adaptation experienced by normal healthy individuals with normal glucose tolerance (NGT).

The illustrated closed-loop infusion system 400 includes a glucose sensor system 410, a control system 412 and an insulin delivery system 414. The glucose sensor system 410 (e.g., sensing arrangement 104) generates a sensor signal 416 representative of blood glucose levels 418 in the body 420, and provides the sensor signal 416 to the control system 412. The control system 412 receives the sensor signal 416 and generates commands 422 that are communicated to the insulin delivery system 414. The insulin delivery system 414 receives the commands 422 and infuses insulin 424 into the body 420 in response to the commands 422.

Generally, the glucose sensor system 410 includes a glucose sensor, sensor electrical components to provide power to the sensor and generate the sensor signal 416, a sensor communication system to carry the sensor signal 416 to the control system 412, and a sensor system housing for the electrical components and the sensor communication system.

Typically, the control system 412 includes controller electrical components and software to generate commands for the insulin delivery system 414 based on the sensor signal 416, and a controller communication system to receive the sensor signal 416 and carry commands to the insulin delivery system 414. In preferred embodiments, the control system 412 is housed in the infusion device housing (e.g., housing 202), however, in alternative embodiments, the control system 412 may be housed independently or in another component of an infusion system (e.g., the sensing arrangement 104, the CCD 106 and/or the computer 108).

The insulin delivery system 414 generally represents the infusion device (e.g., infusion device 102) and any other associated components for infusing insulin 424 into the body 420 (e.g., the motor 232, the gear assembly 236, and the like). In particular embodiments, the infusion device includes infusion electrical components to activate an infusion motor (e.g., motor 232) according to the commands 422, an infusion communication system to receive the commands 422 from the control system 412, and an infusion device housing (e.g., housing 202) to hold the infusion device.

Referring to FIGS. 1-4, in one or more exemplary embodiments, the glucose sensor system 410 samples or otherwise obtains the sensor signal 416, stores the corresponding digital sensor values (Dsig) in a memory and then periodically transmits the digital sensor values Dsig from the memory to the control system 412. The control system 412 processes the digital sensor values Dsig and generates commands 422 for the insulin delivery system 414 to actuate the plunger 222 that forces insulin 424 out of the reservoir 206 the via a fluid communication path from the reservoir to the subcutaneous tissue of the user's body 420.

In preferred embodiments, the control system 412 is designed to model a pancreatic beta cell (β-cell). In other words, the control system 412 commands the infusion device 102, 200 to release insulin 424 into the body 420 at a rate that causes the insulin concentration in the blood to follow a similar concentration profile as would be caused by fully functioning human β-cells responding to blood glucose concentrations in the body 420. In further embodiments, a "semi-closed-loop" system may be used, in which the user is prompted to confirm insulin delivery before any insulin is actually delivered.

Generally, the in vivo β-cell response to changes in glucose is characterized by "first" and "second" phase insulin responses. The biphasic insulin response of a β-cell can be modeled using components of a proportional, plus integral, plus derivative (PID) controller. Accordingly, the control system 412 may be realized as a PID controller since PID algorithms are stable for a wide variety of non-medical dynamic systems, and PID algorithms have been found to be stable over widely varying disturbances and changes in system dynamics.

A proportional component $U_P$ and a derivative component $U_D$ of the PID controller may be combined to represent a first phase insulin response, which lasts several minutes. An integral component $U_I$ of the PID controller represents a second phase insulin response, which is a steady increase in insulin release under hyperglycemic clamp conditions. As described in U.S. patent application Ser. No. 13/966,120, the magnitude of each component's contribution to the insulin response is described by the following equations:

Proportional Component Response: $U_P = K_P(G - G_B)$
Integral Component Response: $U_I = K_I \int_{t_0}^{t} (G - G_B) dt + I_B$, and
Derivative Component Response:

$$U_D = K_D \frac{dG}{dt},$$

Where
$U_P$ is the proportional component of the command sent to the insulin delivery system,
$U_I$ is the integral component of the command sent to the insulin delivery system,
$U_D$ is the derivative component of the command sent to the insulin delivery system,
$K_P$ is a proportional gain coefficient,
$K_I$ is an integral gain coefficient,
$K_D$ is a derivative gain coefficient,
G is a present blood glucose level,
$G_B$ is a desired basal glucose level,
t is the time that has passed since the last sensor calibration,
$t_0$ is the time of the last sensor calibration, and
$I_B$ is a basal insulin concentration at $t_0$, or can also be described as $U_I(t_0)$.

As described in U.S. patent application Ser. No. 13/966,120, the components of the PID controller can also be expressed in discrete form:

Proportional Component Response: $P_{con}^{n} = K_P(SG_f^{n} - G_{sp})$
Integral Component Response: $I_{con}^{n} = I_{con}^{n-1} + K_I(SG_f^{n} - G_{sp})$; $I_{con}^{0} = I_b$
Derivative Component Response: $D_{con}^{n} = K_D dGdt_f^{n}$ Where $K_P$, $K_I$, and $K_D$ are the proportional, integral, and derivative gain coefficients, $SG_f$ and $dGdt_f$ are the filtered sensor glucose and derivative respectively, and the superscript n refers to discrete time.

An acute insulin response is essential for preventing wide postprandial glycemic excursions. Generally, an early insulin response to a sudden increase in glucose level results in less total insulin being needed to bring the glucose level back to a desired basal glucose level. This is because the infusion of insulin increases the percentage of glucose that is taken up by the body. Infusing a large amount of insulin to increase the percentage of glucose uptake while the glucose concentration is high results in an efficient use of insulin. Conversely, infusing a large amount of insulin while the glucose concentration is low results in using a large amount of insulin to remove a relatively small amount of glucose. In other words, a larger percentage of a big number is more than a larger percentage of a small number. The infusion of less total insulin helps to avoid development of insulin resistance in the user. As well, first-phase insulin is thought to result in an early suppression of hepatic glucose output.

Insulin sensitivity is not fixed and can change dramatically in a body depending on the amount of exercise by the body. For example, the insulin response in an exercise-trained individual may be about one-half of the insulin response of an NGT individual, but the glucose uptake rate for the exercise-trained individual may be virtually identical to that of an NGT individual. Thus, an exercise-trained individual may have twice the insulin sensitivity and half of the insulin response leading to the same glucose uptake as an NGT individual. Not only is the first phase insulin response reduced due to the effects of exercise, but the second phase insulin response has also been shown to adjust to insulin sensitivity.

In preferred embodiments, a closed loop control system may be used for delivering insulin to a body to compensate for β-cells that perform inadequately. There is a desired basal blood glucose level $G_B$ for each body. The difference between the desired basal blood glucose level $G_B$ and an estimate of the present blood glucose level G is the glucose level error $G_E$ that must be corrected.

If the glucose level error $G_E$ is positive (meaning that the present estimate of the blood glucose level G is higher than the desired basal blood glucose level $G_B$) then the control system 412 generates an insulin delivery command 422 to drive the infusion device 102, 200 to provide insulin 424 to the body 420. In terms of the control loop, glucose is considered to be positive, and therefore insulin is negative. The sensing arrangement 104, 410 senses the ISF glucose level and generates a sensor signal 416, which, in turn, may be filtered and calibrated to create an estimate of the present blood glucose level. In particular embodiments, the estimate of the present blood glucose level G is adjusted with correction algorithms before it is compared to the desired basal blood glucose level $G_B$ to calculate a new glucose level error $G_E$ to start the loop again.

If the glucose level error $G_E$ is negative (meaning that the present estimate of the blood glucose level is lower than the desired basal blood glucose level $G_B$) then the control system 412 reduces or stops the insulin delivery depending on whether the integral component response of the glucose error $G_E$ is still positive.

If the glucose level error $G_E$ is zero, (meaning that the present estimate of the blood glucose level is equal to the desired basal blood glucose level $G_B$) then the control system 412 may or may not issue commands to infuse insulin depending on the derivative component (whether the glucose level is raising or falling) and the integral component (how long and by how much glucose level has been above or below the basal blood glucose level $G_B$). In "semi-closed loop" embodiments, the user is prompted before the control system 412 issues the commands to infuse insulin. The prompts may be displayed to the user on a display, sounded to the user, or otherwise provide an indication to the user that the system is ready to deliver insulin, for example a vibration or other tactile indication. In addition, the amount of insulin to be delivered may be displayed, with or without other information, such as the total amount infused for the day or the potential effect on the user's blood glucose level by the insulin delivery. In response, the user may indicate that the insulin should or should not be delivered, for example by selecting a button, key, or other input. In further embodiments, there must be at least two keystrokes so that insulin is not delivered by accident.

Figure 5:
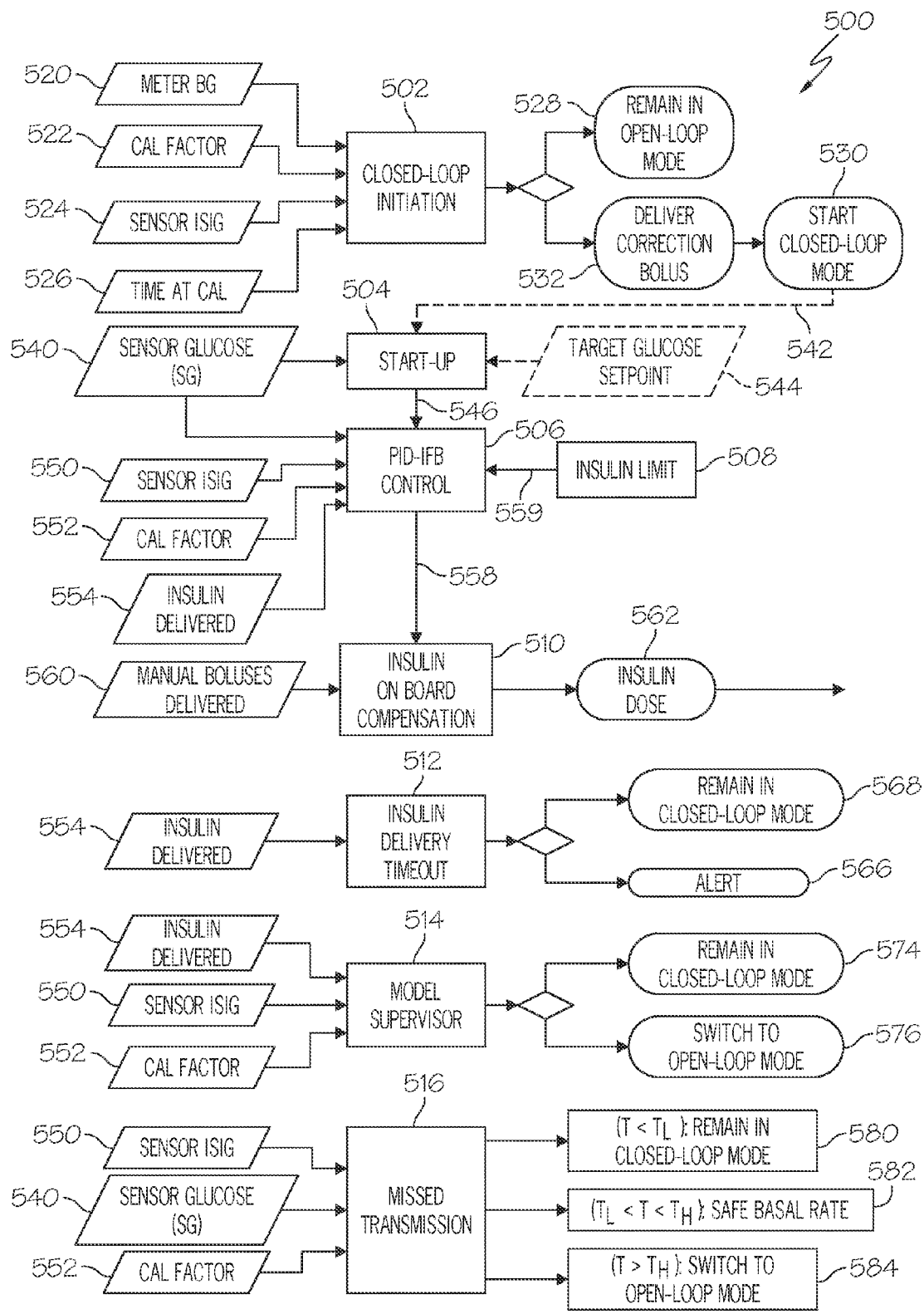
FIG. 5 is a block diagram that illustrates processing modules and algorithms of an exemplary embodiment of a control system suitable for use with the closed-loop infusion system of FIG. 4.
Figure 6:
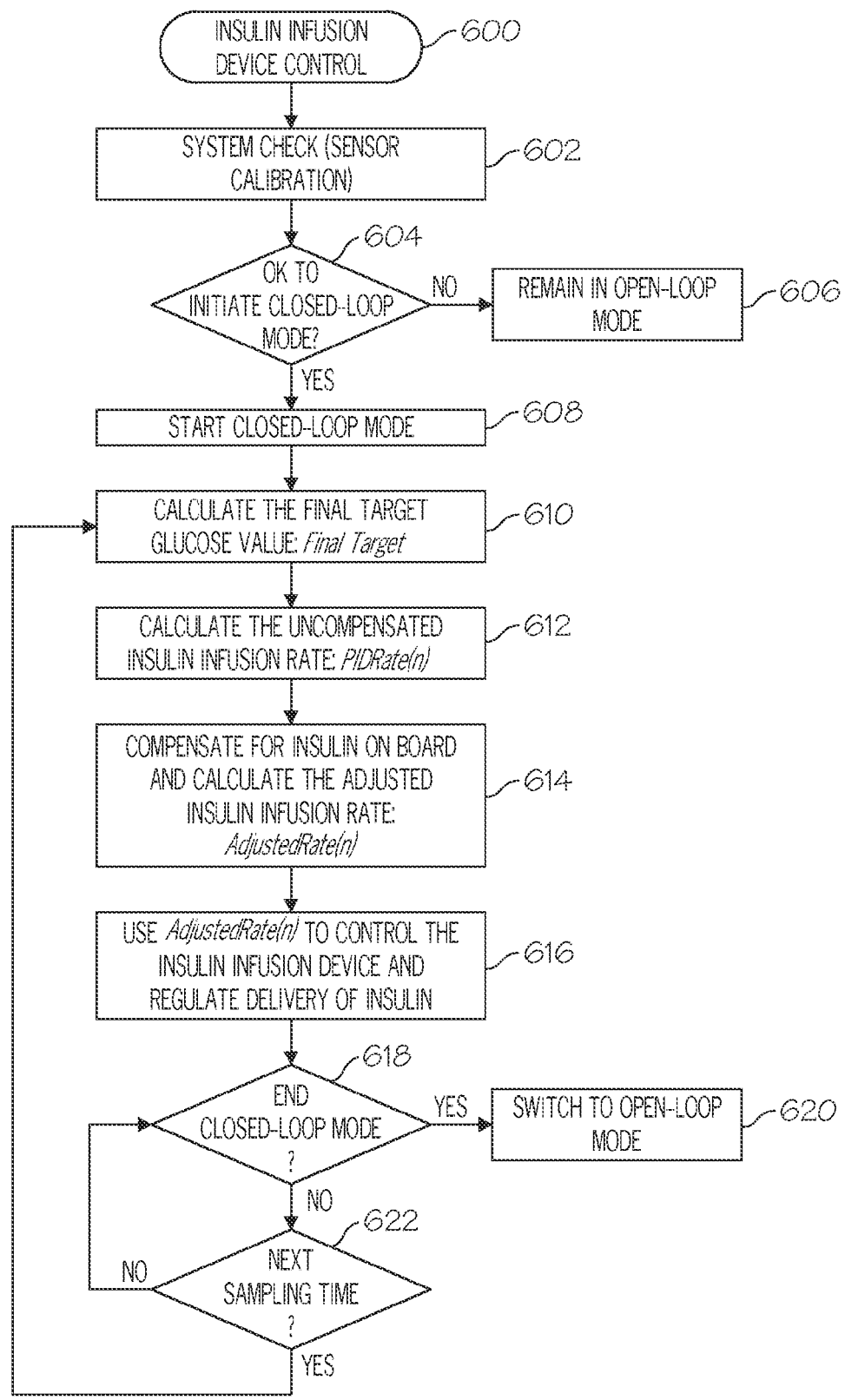
FIG. 6 is a flow diagram of an exemplary control process suitable for use with the control system of FIG. 5.

FIG. 5 depicts a block diagram that illustrates processing modules and algorithms of an exemplary embodiment of a control system 500 suitable for use as the control system 412 in the infusion system 400 of FIG. 4, and FIG. 6 is a flow chart that illustrates an exemplary embodiment of a control process 600 that may be performed at least in part by the control system 500 to control the insulin delivery system 414 (e.g., motor 232).

FIG. 5 schematically depicts certain inputs and outputs of the control system 500, where the parallelograms represent the inputs, the ovals represent the outputs, and the rectangles represent the various functional modules of the control system 500. In the context of this description, a "functional module" may be any process, technique, method, algorithm, computer-executable program logic, or the like. In this regard, the control system 500 could be realized as any electronic device having a processor architecture with at least one processor device, and at least one memory element that is cooperatively associated with the processor architecture. The processor architecture is suitably configured to execute processor-executable instructions stored in the at least one memory element such that the control system 500 can perform the various control operations and methods described in detail herein. Although FIG. 5 conveniently depicts a number of separate functional modules, it should be appreciated that the overall functionality and configuration of the control system 500 may be alternatively arranged, and that the functions, operations, and tasks described herein may be performed by one or more of the modules as needed.

The host electronic device that implements the control system 500 may be realized as a monitor device for an insulin infusion device, where the monitor device and the insulin infusion device are two physically distinct hardware devices. In another embodiment of the system, the host electronic device that implements the control system 500 may be realized as a portable wireless device, where the portable wireless device and the insulin infusion device are two physically distinct hardware devices. The portable wireless device in this context may be, without limitation: a mobile telephone device; a tablet computer device; a laptop computer device; a portable video game device; a digital media player device; a portable medical device; or the like. In yet other system embodiments, the host electronic device and the insulin infusion device are physically and functionally integrated into a single hardware device. In such embodiments, the insulin infusion device will include the functionality of the control system 500 as presented here.

Certain embodiments of the control system 500 include a plurality of cooperating functional modules that are designed and configured to determine the insulin dose to be delivered to keep the patient at the target glucose setpoint during an overnight closed-loop operating mode. In this regard, the illustrated embodiment of the control system 500 may include the following functional modules, without limitation: a closed-loop initiation module 502; a start-up module 504; a proportional integral derivative insulin feedback (PID-IFB) control module 506; an insulin limit module 508; an insulin on board (IOB) compensation module 510; an insulin delivery timeout module 512; a model supervisor module 514; and a missed transmission module 516.

Referring to FIG. 6, the control process 600 may begin at any time when it is desired to enter the closed-loop operating mode. Accordingly, the control process 600 may begin in response to a user-initiated command, automatically in response to the detection of operating conditions that are usually indicative of closed-loop operation (e.g., sleeping), or the like. Certain embodiments of the control process 600 may begin with one or more system checks (task 602) to confirm whether or not the system is allowed to enter the closed-loop operating mode. This particular example employs a sensor calibration check before allowing the system to proceed to the closed-loop mode. Referring to FIG. 5, the closed-loop initiation module 502 may be involved during task 602.

In some embodiments, the closed-loop initiation module 502 may consider certain sensor performance criteria that prevents closed-loop initiation. Such criteria may include, without limitation: (1) during start-up when the calibration is not stable; (2) when the sensor sensitivity changes significantly; (3) when sensors may be calibrated with a potentially invalid meter reading thereby changing the sensor sensitivity significantly; (4) any other situation that could cause a mismatch between the sensor and meter for a number of most recent calibrations spaced over a designated period of time (e.g., the two most recent calibrations).

The illustrated embodiment of the closed-loop initiation module 502 receives at least the following items as inputs: a meter (measured) BG value 520; at least one sensor calibration factor 522 (i.e., calibration measurements, calibration data, etc.); the sensor Isig value 524; and timestamp data 526 that indicates the calibration time associated with the BG value 520 and the sensor calibration factor 522. Some or all of this input data may be provided directly or indirectly by the insulin delivery system 414 (see FIG. 4), a translator device, a monitor device, or any device in the closed-loop system. This description assumes that a new sensor calibration factor 522 and new timestamp data 526 is generated for each measured BG value 520, wherein the sensor calibration factor 522 is associated with the calibration of the glucose sensor system 410 (see FIG. 4) that is being used to monitor the patient. In particular, the sensor calibration factor may be based on the meter BG value 520 and the corresponding sensor Isig value 524.

The closed-loop initiation module 502 analyzes the input data (both current values and historical values) to determine whether or not the system is allowed to enter into the closed-loop mode. For example, the closed-loop initiation module 502 may: check the period between two consecutive calibration timestamp values; compare recent and prior calibration factor values; and the like. The "outputs" of the closed-loop initiation module 502 correspond to two operating modes of the system. More specifically, the closed-loop initiation module 502 controls whether the system remains operating in the open-loop mode 528 or whether the system starts the closed-loop mode 530.

Referring to FIG. 6, if the closed-loop mode is not permitted (the "No" branch of query task 604), then the control process 600 operates the system such that it remains in the open-loop mode (task 606). On the other hand, if the closed-loop mode is permitted (the "Yes" branch of query task 604), then the control process 600 can initiate and start the closed-loop mode in an appropriate manner (task 608). Referring again to FIG. 5, a correction bolus 532 can be calculated and delivered (if needed) to mitigate hyperglycemia at the commencement of the closed-loop mode. This correction bolus 532 serves as an additional safeguard to achieve a target blood glucose level if a measured meter reading is greater than a threshold value. If the control process 600 determines that a correction bolus is required, then an appropriate insulin dose instruction is generated for execution by the insulin delivery system at the outset of the closed-loop mode.

Referring to FIG. 5, the start-up module 504 may be called in response to a determination that the system can proceed to the closed-loop operating mode. Once the system is in the closed-loop operating mode, the controller retrieves historical data that can be processed and used as described in more detail below. In one or more embodiments, for example, the controller obtains data for the last 24 hours (from the insulin delivery system, from a monitor, or the like). Thereafter, the controller retrieves data packets once every sampling period to obtain, without limitation: sensor glucose (SG) values; sensor Isig values; sensor calibration factors; information related to the amount of insulin delivered; information related to manual boluses delivered; and sensor calibration factors. As explained in more detail below, the received information can be used in the various safeguards, and to determine the final insulin dose.

The start-up module 504 receives sensor glucose (SG) values 540 as an input, and the functionality of the start-up module 504 may be initiated in response to the start of the closed-loop mode 530 (this trigger mechanism is represented by the dashed arrow 542 in FIG. 5). The SG values 540 may be provided directly by the glucose sensor system 410 or indirectly via the insulin delivery system 414, a translator device, or any device in the closed-loop system (see FIG. 4). This description assumes that SG values 540 are received by the start-up module 504 in an ongoing manner as they become available. The start-up module 504 may also utilize a target glucose setpoint value 544, which may be internally maintained, generated, and/or provided by the control system 500. For the implementation presented here, the target glucose setpoint value 544 represents a fixed (constant) value that the user can specify (FIG. 5 depicts the target glucose setpoint value 544 in dashed lines to indicate that the value is a user-specified parameter rather than a functional module or data received by the system).

In certain embodiments, the start-up module 504 calculates a final target glucose value 546, which serves as an input to the PID-IFB control module 506. The final target glucose value 546 enables the system to make a smoother transition between open-loop and closed-loop modes (by gradually adjusting the final target glucose value 546). The start-up module 504 may utilize the target glucose setpoint value 544 to calculate the final target glucose value 546. In this regard, the start-up module 504 elevates the final target glucose value 546 to the same level as the sensor glucose value at the start of the closed-loop mode, provided the sensor glucose is above a certain threshold. As time progresses, the final target glucose value 546 gradually decreases back to the target glucose setpoint value 544 (usually in approximately two hours). Referring to FIG. 6, the control process 600 calculates the final target glucose value (task 610) and continues by calculating an uncompensated insulin infusion rate, PIDRate(n), based at least in part on the final target glucose value (task 612). For this example, the start-up module 504 may be involved during task 610, and the PID-IFB control module 506 may be involved during task 612.

As an additional safeguard, the insulin limit module 508 cooperates with the PID-IFB control module 506 to provide an upper insulin limit that is calculated based on the patient's insulin intake during a designated fasting period, the patient's fasting blood glucose, and the patient's insulin sensitivity. This insulin limit imposes an upper limit to the insulin delivery rate to avoid over-delivery of insulin by the system due to potential sensor error.

The PID-IFB control module 506 may be configured to carry out the control processes described above with reference to FIG. 4. In some embodiments, the PID-IFB control module 506 receives at least the following items as inputs: the SG value 540 (which may be used to calculate a rate of change value that indicates the rate of change of the SG value); the current sensor Isig value 550; the current sensor calibration factor 552; and an amount of insulin delivered 554. As shown in FIG. 5, the PID-IFB control module 506 may also receive an insulin limit 559 (e.g., a maximum insulin infusion rate) for the user, as calculated by the insulin limit module 508. The inputs to the PID-IFB control module 506 may be provided directly or indirectly by the insulin delivery system 414, the glucose sensor system 410, a translator device, a monitor device, and/or any device in the closed-loop system (see FIG. 4). The PID-IFB control module 506 is suitably configured to calculate the insulin infusion rate based on the current and past SG values 540, the SG rate of change, the sensor Isig value 550, the sensor calibration factor 552, the final target glucose value 546, and the insulin delivered 554 in order to achieve euglycemia. These (and possibly other) values may be received by the PID-IFB control module 506 in an ongoing manner as they become available, e.g., in five minute intervals or in accordance with any desired schedule.

The insulin delivered 554 is a parameter or value that indicates the amount of insulin that has been delivered to the patient by the insulin delivery system. Thus, the insulin delivered 554 may indicate recent boluses (typically by Units) delivered over a period of time. In certain implementations, the insulin delivered 554 corresponds to the amount of insulin delivered in the last sampling time, which may be, without limitation: one minute; five minutes; thirty seconds; or any designated sampling time. The insulin delivered 554 may also indicate the amount of insulin delivered by the delivery system as basal or boluses in any defined period of time in the past (e.g., the last N hours) or the amount of insulin delivered by the system in the last sampling cycle. In practice, the PID-IFB control module 506 (and the IOB compensation module 510) may be "initialized" to collect and save historical values for the insulin delivered 554 as needed. Thereafter, the insulin delivered 554 can simply indicate an amount of insulin administered by the system during the last sampling time period if by a bolus or basal channels.

As mentioned above, the PID-IFB control module 506 may utilize the upper insulin limit 559, which is a patient-specific parameter. In certain embodiments, the upper insulin limit 559 may be entered by the user, a caregiver, or the like. Alternatively, the insulin limit module 508 may be responsible for calculating or otherwise managing the upper insulin limit 559 if so desired. The upper insulin limit 559 imposes an upper limit to the insulin delivery rate as an additional safety feature to avoid over-delivery of insulin by the control system 500 due to potential sensor error. Thus, if the PID-IFB control module 506 recommends a dose higher than the insulin limit 559, the insulin limit 559 will be utilized to constrain the insulin delivered to the insulin limit value. In addition, implementation of the insulin limit 559 will "freeze" the integral component of the PID to its previous value to prevent integral windup, which can cause continuous integrating of the glucose error until it reaches maximum values. In certain embodiments, the upper insulin limit 559 has a default value set at five times the patient's basal rate. Hence, if the maximum value is reached, the PID-IFB control algorithm will be fairly aggressive in calculating an insulin dose. Accordingly, to minimize integral windup, the insulin limit 559 is fed back to the PID-IFB control module 506 (as depicted in FIG. 5) for use in the next insulin dose calculation.

The PID-IFB control module 506 operates as described previously to calculate a current insulin dose 558 as an output value (the current insulin dose 558 is also referred to herein as the uncompensated insulin infusion rate, PIDRate(n)). In practice, the current insulin dose 558 is typically expressed as an infusion rate (Units/Hour). In the context of this description, the current insulin dose 558 may represent a closed-loop infusion rate that has already been subjected to limiting by the insulin limit module 508, and which may be subjected to further adjustment or compensation by the IOB compensation module 510. Thus, the output of the insulin limit module 508 (the upper insulin limit 559) represents a potentially limited insulin dose to be provided by the PID-IFB control module 506—if no limit is imposed, then the insulin limit 559 has no effect on the output of the PID-IFB control module 506; otherwise, the current insulin dose 558 will be the same as the upper insulin limit 559. Referring again to FIG. 6, the control process 600 may compensate for the insulin "on board" the patient by calculating an adjusted insulin infusion rate, AdjustedRate(n), based at least in part on the uncompensated insulin infusion rate (task 614). For this example, the IOB compensation module 510 may be involved during task 614.

The IOB compensation module 510 receives at least the following items as inputs: the current insulin dose 558; and information regarding manual boluses delivered 560. The manual boluses delivered 560 may be provided directly or indirectly by the insulin delivery system 414, a translator device, a monitor device, and/or any device in the closed-loop system (see FIG. 4). This description assumes that the manual boluses delivered 560 is received by the IOB compensation module 510 in an ongoing manner as it becomes available, e.g., in five minute intervals or in accordance with any desired schedule. The IOB compensation module 510 is suitably configured to estimate insulin on board based on manual boluses delivered, before or during closed-loop operation, in order to compensate the final infusion rate to help avoid over-delivery of insulin by the control system 500. Accordingly, the output of the IOB compensation module 510 may be a final insulin dose 562 expressed as a final infusion rate (Units/Hour). The final insulin dose 562 is also referred to herein as the adjusted insulin infusion rate, AdjustedRate(n).

Referring to FIG. 6, the control process 600 uses the adjusted insulin infusion rate, AdjustedRate(n), to control the insulin infusion device, which in turn regulates the delivery of insulin to the body of the user (task 616). In certain embodiments, the adjusted insulin infusion rate is communicated to the insulin infusion device in an appropriate manner (such as wireless data communication). The control process 600 may continue as described above in an iterative and ongoing manner to monitor the condition of the user and deliver insulin as needed without user involvement. That said, if the control process 600 determines that the closed-loop operating mode should be terminated (the "Yes" branch of query task 618), then the control process 600 causes the system to switch back to the open-loop mode (task 620). The closed-loop mode may be ended in response to a user-initiated command, automatically in response to the detection of operating conditions that are usually indicative of open-loop operation, or the like.

If query task 618 determines that the closed-loop mode should continue (the "No" branch of query task 618), then the control process 600 may check whether it is time to perform another iteration of the control routine. In other words, the control process 600 may check for the next sampling time (query task 622). If it is time for the next iteration, then the control process 600 may return to task 610 and repeat the computations with the next set of data values. For example, the next iteration of the control routine may obtain and process the current values of some or all of the following parameters, without limitation: the SG value 540; the SG rate of change; the sensor Isig value 524; the amount of insulin delivered 554; and the manual boluses delivered 560. This allows the control process 600 to adjust the final insulin infusion rate in an ongoing manner in accordance with a predetermined schedule, a designated sampling rate, or the like.

The insulin delivery timeout module 512 monitors if the patient is receiving continuous delivery of insulin at the maximum insulin limit or the minimum allowable infusion of zero Units/Hour for a time specified by the controller. Accordingly, the insulin delivery timeout module 512 may receive the insulin delivered 554 as an input. If the specified time is exceeded, the system will trigger a fail-safe alert 566. Otherwise, the system remains in the closed-loop operating mode 568.

Referring back to FIG. 5, the model supervisor module 514 receives at least the following as inputs: the insulin delivered 554; sensor Isig values 550; and one or more sensor calibration factors 552. The inputs to the model supervisor module 514 may be provided directly or indirectly by the insulin delivery system 414, the glucose sensor system 410, a translator device, a monitor device, and/or any device in the closed-loop system (see FIG. 4). The model supervisor module 514 is suitably designed and configured to estimate the user's glucose concentration in real time (or substantially real time) based on the insulin delivered 554, the sensor Isig values 550, and the sensor calibration factors 552. The sensor calibration factors 552 used by the model supervisor module 514 are equal to the sensor calibration factors 522 used by the closed-loop initiation module 502. That said, the closed-loop initiation module 502 utilizes the sensor calibration factors 522 at one particular time, whereas the model supervisor module 514 considers the sensor calibration factors 552 in an ongoing and continuous manner during operation in the closed-loop mode. Should the model-predicted glucose and the sensor glucose values differ significantly, the system will exit closed loop mode. Accordingly, the model supervisor module 514 regulates whether the system remains in the closed-loop mode 574 or switches to the open-loop mode 576.

The missed transmission module 516 is suitably configured to monitor the following, without limitation: the sensor Isig values 550; the SG values 540; and the sensor calibration factors 552. More particularly, the missed transmission module 516 continuously monitors to check whether the system is receiving data packets that convey the necessary information and input values. For missed data packets totaling less than a lower threshold of time (e.g., 15 minutes), the system remains in the closed-loop mode, as indicated by block 580 in FIG. 5. During this time, the system will continue to calculate the insulin dose using the closed-loop control methodology based on the last valid sensor glucose value. For missed data packets totaling a time longer than the lower threshold and shorter than an upper threshold of time (e.g., 60 minutes), the missed transmission module 516 will switch the system to a pre-programmed safe basal rate, as indicated by block 582 in FIG. 5. In certain embodiments, this safe basal rate is defined as half the patient's overnight basal rate, and this parameter may be programmed by a caregiver or physician. If the missed transmission module 516 starts receiving data packets while the safe basal rate is being administered, the system will switch back to the closed-loop mode. For missed data packets totaling more than the upper threshold of time, the system will switch to the open-loop mode, as indicated by block 584 in FIG. 5. At this point, the system will be controlled to deliver a pre-programmed open-loop overnight basal rate.

To summarize, the control system 500 determines whether to enter into the closed-loop mode in response to at least the recent meter BG values 520, the sensor calibration factors 522, and the calibration timestamp data 526. The control system 500 utilizes the closed-loop initiation module 502 to check if the sensor calibration time between the last two calibration values is within an acceptable range, and whether any change between the two calibration values (recent and prior value) is acceptable. If so, the control system 500 will switch the system into the closed-loop mode. Once the system is in the closed-loop mode, the control system 500 will periodically receive data packets (e.g., every five minutes) that include the current SG value 540, the current sensor Isig values 550, the insulin delivered 554, the sensor calibration factors 552, and manual boluses delivered 560. In certain embodiments, each of the data packets received by the control system 500 includes data collected during the previous 24-hour period.

The start-up module 504 utilizes the SG values 540 and the target glucose setpoint value 544 to calculate the final target glucose value 546. In some embodiments, the target glucose setpoint value 544 is set to 120 mg/dL, although other settings could be used if so desired (a typical range of settings may be, for example 70-300 mg/dL). This results in a smoother transition between open-loop and closed-loop modes by gradually adjusting the final target glucose value 546. The final target glucose value 546 is sent to the PID-IFB control module 506 for use as one input that influences the calculation of the final insulin dose 562.

The PID-IFB control module 506 utilizes the final target glucose value 546, the current and past SG values 540, the SG rate of change values, and the insulin delivered 554 to determine the insulin infusion rate (the current insulin dose 558) in order to achieve euglycemia. As an additional safeguard, the upper insulin limit 559 (calculated based on the patient's insulin intake during a fasting period, fasting blood glucose, and insulin sensitivity) from the insulin limit module 508 is input into the control system 500 for each patient to impose an upper limit to the insulin delivery rate to avoid over-delivery of insulin by the control system 500. The PID-IFB control module 506 considers the upper insulin limit 559 before sending the current insulin dose 558 to the IOB compensation module 510, which estimates insulin on board from manual boluses, before or during closed-loop operation, in order to calculate the final insulin dose 562. The final insulin dose 562 may be communicated from the control system 500 directly or indirectly to the insulin delivery system 414 such that the final insulin dose 562 can be delivered to the patient during closed-loop operation.

Additional safeguards could be implemented to monitor the system during closed-loop operation, such that the system exits the closed-loop mode when certain criteria are not met. For example, the control system 500 may cause the system to exit the closed-loop mode if more than a designated number of consecutive data packets are missed. This assumes that the control system 500 usually receives data packets (from the insulin delivery system 414, from a monitor, from a translation device, or the like) in a continuous manner during closed-loop operation. Thus, if the control system 500 detects that more than a threshold number of consecutive data packets are not received as expected, the system will be commanded to exit the closed-loop mode. This functionality is associated with the missed transmission module 516, as described previously.

Moreover, the model supervisor module 514 estimates the user's glucose concentration in an ongoing manner, based on the insulin delivered 554, the sensor Isig values 550, and the sensor calibration factors 552. If the difference between the model-predicted glucose and the sensor glucose value is greater than a stated threshold, the control system 500 may cause the system to exit the closed-loop mode.

As summarized above, the control system 500 employs a number of modules or functions that cooperate to regulate the delivery of insulin during closed-loop operation: the closed-loop initiation module 502; the start-up module 504; the PID-IFB control module 506; the insulin limit module 508; and the IOB compensation module 510. Moreover, the control system 500 may employ a number of modules that perform various safeguarding functions during closed-loop operation. These safeguarding modules may include: the insulin delivery timeout module 512; the model supervisor module 514; and the missed transmission module 516.

Figure 7:
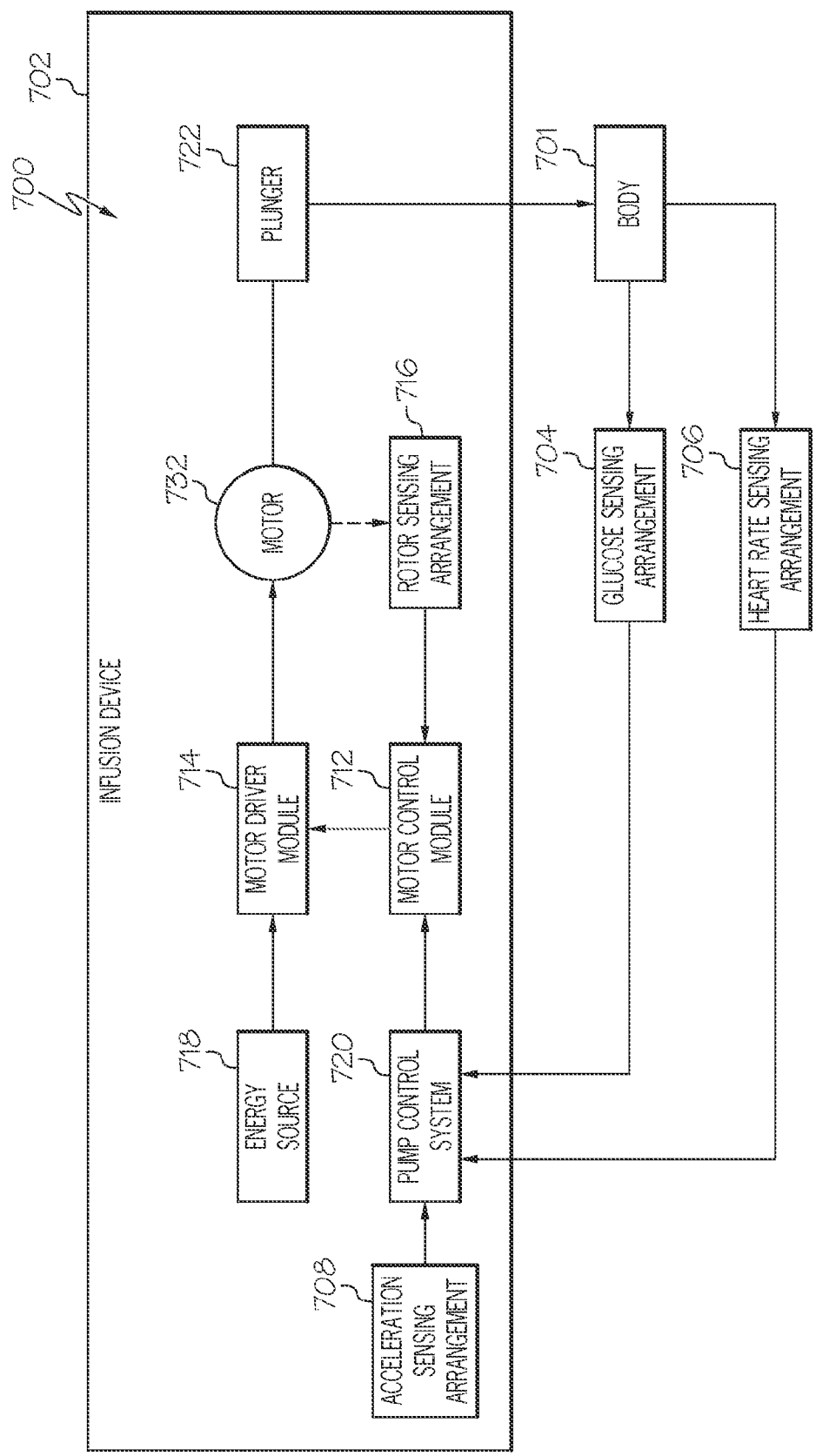
FIG. 7 is a block diagram of an exemplary infusion system suitable for use with the closed-loop infusion system of FIGS. 4-6

FIG. 7 depicts another exemplary embodiment of an infusion system 700 suitable for use with an infusion device 702, such as the infusion device 102 in FIG. 1 or the infusion device 200 of FIG. 2 in conjunction with the closed-loop infusion system 400 of FIG. 4 and the closed-loop control process 600 of FIG. 6. In this regard, the illustrated infusion system 700 is capable of operating the infusion device 702 to control or otherwise regulate a condition in the body 701 of a user, such as the blood glucose level, to a desired (or target) value or otherwise maintain the condition within a range of acceptable values. A sensing arrangement 704 (e.g., sensing arrangement 104) is communicatively coupled to the infusion device 702, and in exemplary embodiments, the sensing arrangement 704 is configured to sense, detect, measure or otherwise quantify the condition being regulated in the body 701 of the user. However, it should be noted that in alternative embodiments, the condition being regulated by the infusion system 700 may be correlative to the measured values obtained by the sensing arrangement 704. That said, for clarity and purposes of explanation, the subject matter may be described herein in the context of the sensing arrangement 704 being realized as a blood glucose sensing arrangement that senses, detects, measures or otherwise quantifies the blood glucose level being regulated in the body 701 of the user.

In exemplary embodiments, the infusion system 700 includes one or more additional sensing arrangements 706, 708 configured to sense, detect, measure or otherwise quantify a characteristic of the body 701 of the user that is indicative of a condition in the body 701 of the user that is likely to influence the response by the user's body 701 to the fluid being delivered. For example, in the illustrated embodiment, the infusion system 700 includes a heart rate sensing arrangement 706 that may be worn on or otherwise associated with the user's body 701 to sense, detect, measure or otherwise quantify the user's heart rate, which, in turn, may be indicative of exercise, stress, or some other condition in the body 701 that is likely to influence the user's insulin response in the body 701. The measured heart rate values output by the heart rate sensing arrangement 706 may be utilized by the pump control system 720 to calculate or otherwise quantify one or more characteristics of the user's heart rate, such as the user's heart rate variability (HRV) or the like. Alternatively, the heart rate sensing arrangement 706 may sense, detect, measure or otherwise quantify characteristics of the user's heart rate (e.g., the user's HRV) and output those values in addition to measured heart rate values. While the illustrated embodiment depicts the heart rate sensing arrangement 706 as being realized as a standalone component worn by the user, in alternative embodiments, the heart rate sensing arrangement 706 may be integrated with the infusion device 702 or with another sensing arrangement 704, 708 worn on the body 701 of the user.

Additionally, the illustrated infusion system 700 includes an acceleration sensing arrangement 708 (or accelerometer) that may be worn on or otherwise associated with the user's body 701 to sense, detect, measure or otherwise quantify an acceleration of the user's body 701, which, in turn, may be indicative of exercise or some other condition in the body 701 that is likely to influence the user's insulin response. In the illustrated embodiment, the acceleration sensing arrangement 708 is depicted as being integrated into the infusion device 702, however, in alternative embodiments, the acceleration sensing arrangement 708 may be integrated with another sensing arrangement 704, 706 on the body 701 of the user, or the acceleration sensing arrangement 708 may be realized as a standalone component that is worn by the user.

In the illustrated embodiment, the pump control system 720 generally represents the electronics and other components of the infusion device 702 that control operation of the fluid infusion device 702 according to a desired infusion delivery program in a manner that is influenced by sensor data pertaining to a condition of a user (e.g., the user's current glucose level) received from the glucose sensing arrangement 704 and/or in a manner that is dictated by the user. To support closed-loop control, the pump control system 720 maintains, receives, or otherwise obtains a desired value for a condition in the body 701 of the user to be regulated (e.g., a target or commanded blood glucose value). For example, the infusion device 702 may store or otherwise maintain the target value in a data storage element accessible to the pump control system 720. Alternatively, the target value may be received from an external component (e.g., CCD 106 and/or computer 108) or be input by a user via a user interface associated with the infusion device 702.

As described in greater detail below in the context of FIGS. 9-10, in exemplary embodiments, the pump control system 720 is coupled to the sensing arrangements 706, 708 to obtain measurement data indicative of the respective characteristics of the body 701 of the user from the respective sensing arrangements 706, 708. Based on the measurement data, the pump control system 720 detects or otherwise identifies a condition being experienced by the body 701 of the user that is likely to influence the user's insulin response. The pump control system 720 also utilizes the measurement data to identify or otherwise classify the detected insulin sensitivity condition as a particular type of a plurality of possible types of conditions that are likely to influence the user's insulin response. For example, based on the heart rate measurement data obtained from the heart rate sensing arrangement 706 and the acceleration measurement data obtained from the acceleration sensing arrangement 708, the pump control system 720 may identify or otherwise determine whether the body 701 of the user is experiencing exercise or stress. Based on the identified type of insulin sensitivity condition in the body 701, the pump control system 720 automatically adjusts or otherwise modifies at least some of the closed-loop control information for operating the infusion device 702 in a manner that accounts for the anticipated change in the user's insulin response likely to be caused by the identified condition. Thereafter, the pump control system 720 operates the infusion device 702 to provide closed-loop control in accordance with the adjusted control information. For example, as described in greater detail below, the pump control system 720 may adjust one or more PID gain coefficients, one or more insulin delivery limits, one or more PID blood glucose targets, one or more time limits for the closed-loop control, or the like.

Still referring to FIG. 7, the infusion device 702 includes a motor control module 712 coupled to a motor 732 (e.g., motor 232) that is operable to displace a plunger 722 (e.g., plunger 222) in a reservoir (e.g., reservoir 206) and provide a desired amount of fluid to the body 701 of a user. In this regard, displacement of the plunger 722 results in the delivery of a fluid that is capable of influencing the condition in the body 701 of the user via a fluid delivery path. A motor driver module 714 is coupled between an energy source 718 and the motor 732. The motor control module 712 is coupled to the motor driver module 714, and the motor control module 712 generates or otherwise provides command signals that operate the motor driver module 714 to provide current (or power) from the energy source 718 to the motor 732 to displace the plunger 722 in response to receiving, from a pump control system 720, a delivery command (or dosage command) indicative of the desired amount of fluid to be delivered.

In exemplary embodiments, the energy source 718 is realized as a battery housed within the infusion device 702 (e.g., within housing 202) that provides direct current (DC) power. In this regard, the motor driver module 714 generally represents the combination of circuitry, hardware and/or other electrical components configured to convert or otherwise transfer DC power provided by the energy source 718 into alternating electrical signals applied to respective phases of the stator windings of the motor 732 that result in current flowing through the stator windings that generates a stator magnetic field and causes the rotor of the motor 732 to rotate. The motor control module 712 is configured to receive or otherwise obtain a delivery command (or commanded dosage) from the pump control system 720, convert the delivery command to a commanded translational displacement of the plunger 722, and command, signal, or otherwise operate the motor driver module 714 to cause the rotor of the motor 732 to rotate by an amount that produces the commanded translational displacement of the plunger 722. For example, the motor control module 712 may determine an amount of rotation of the rotor required to produce translational displacement of the plunger 722 that achieves the commanded dosage received from the pump control system 720.

Based on the current rotational position (or orientation) of the rotor with respect to the stator that is indicated by the output of the rotor sensing arrangement 716, the motor control module 712 determines the appropriate sequence of alternating electrical signals to be applied to the respective phases of the stator windings that should rotate the rotor by the determined amount of rotation from its current position (or orientation). In embodiments where the motor 732 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 712 operates the motor driver module 714 to apply the determined alternating electrical signals (e.g., the command signals) to the stator windings of the motor 732 to achieve the desired delivery of fluid to the user. When the motor control module 712 is operating the motor driver module 714, current flows from the energy source 718 through the stator windings of the motor 732 to produce a stator magnetic field that interacts with the rotor magnetic field. In some embodiments, after the motor control module 712 operates the motor driver module 714 and/or motor 732 to achieve the commanded dosage, the motor control module 712 ceases operating the motor driver module 714 and/or motor 732 until a subsequent delivery command is received. In this regard, the motor driver module 714 and the motor 732 enter an idle state during which the motor driver module 714 effectively disconnects or isolates the stator windings of the motor 732 from the energy source 718. In other words, current does not flow from the energy source 718 through the stator windings of the motor 732 when the motor 732 is idle, and thus, the motor 732 does not consume power from the energy source 718 in the idle state, thereby improving efficiency.

Depending on the embodiment, the motor control module 712 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 712, or in any practical combination thereof. In exemplary embodiments, the motor control module 712 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 712. The computer-executable programming instructions, when read and executed by the motor control module 712, cause the motor control module 712 to perform the tasks, operations, functions, and processes described herein.

It should be understood that FIG. 7 depicts a simplified representation of the infusion device 702 for purposes of explanation and is not intended to limit the subject matter described herein in any way. In this regard, depending on the embodiment, some features and/or functionality of the motor control module 712 may implemented by or otherwise integrated into the pump control system 720, or vice versa. Furthermore, some of the features and/or functionality of the pump control system 720 described herein may be implemented by a remote computing device that is physically distinct and/or separate from the infusion device 702 (e.g., the CCD 106, the computer 108, and/or another monitor device) and communicatively coupled to the motor control module 712 and/or the sensing arrangements 704, 706, 708. Additionally, although FIG. 7 depicts the glucose sensing arrangement 704 as being physically separate and distinct from the infusion device 702, in alternative embodiments, the glucose sensing arrangement 704 may be integrated into or otherwise implemented by the infusion device 702 (e.g., by providing the glucose sensing arrangement 704 within the housing 202).

Figure 8:
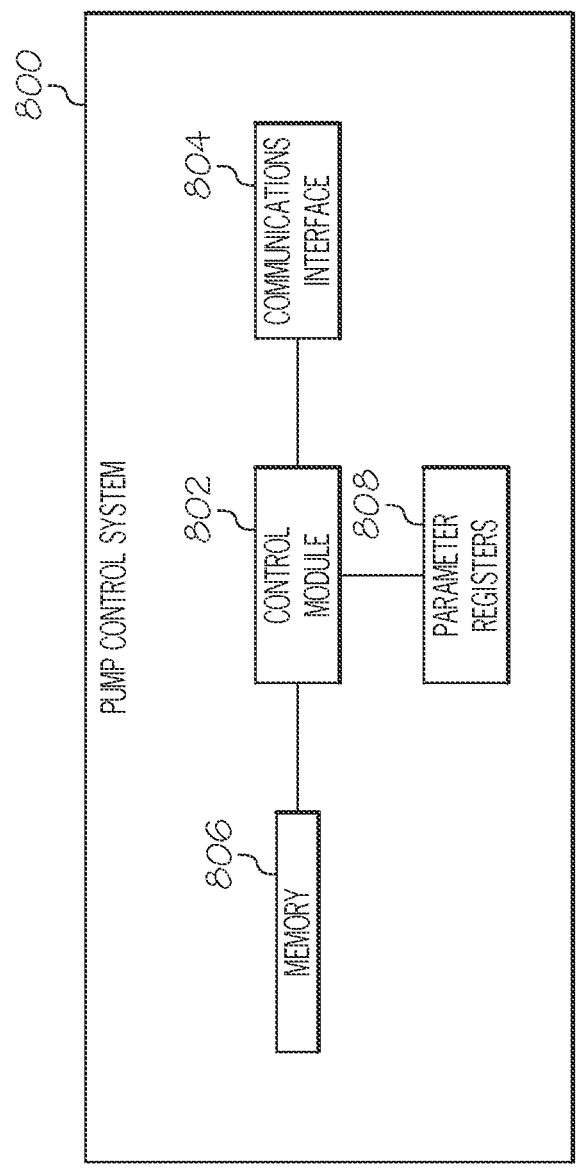
FIG. 8 is a block diagram of an exemplary pump control system suitable for use in the infusion system of FIG. 7.

FIG. 8 depicts an exemplary embodiment of a pump control system 800 suitable for use as the pump control system 720 in FIG. 8 in accordance with one or more embodiments. The illustrated pump control system 800 includes, without limitation, a pump control module 802, a communications interface 804, and data storage elements 806, 808. It should be understood that FIG. 8 is a simplified representation of pump control system 800 for purposes of explanation and is not intended to limit the subject matter described herein in any way. In this regard, although FIG. 8 depicts the data storage elements 806, 808 as being distinct or otherwise separate from one another, in practice, the data storage elements 806, 808 may be realized using a single integrated data storage element.

The control module 802 generally represents the hardware, circuitry, logic, firmware and/or other components of the pump control system 800 configured to determine delivery (or dosage) commands for operating a motor using closed-loop control and perform various additional tasks, operations, functions and/or operations described herein. Depending on the embodiment, the control module 802 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the control module 802, or in any practical combination thereof In exemplary embodiments, the data storage element (or memory) 806 is realized as any sort of random access memory (RAM), read only memory (ROM), flash memory, registers, hard disks, removable disks, magnetic or optical mass storage, short or long term storage media, or any other non-transitory computer-readable medium capable of storing programming instructions for execution by the control module 802. The computer-executable programming instructions, when read and executed by the control module 802, cause the control module 802 to perform the tasks, operations, functions, and processes described in greater detail below. In this regard, the control scheme or algorithm implemented by the control module 802 may be realized as control application code that is stored or otherwise maintained in the memory 806 and executed by the control module 802 to implement or otherwise provide one or more of the closed-loop PID control components in software. For example, the control application code may be executed by the control module 802 to implement or otherwise provide one or more of the components of control system 500 of FIG. 5 and implement the control process 600 of FIG. 6.

As described above with reference to FIGS. 4-7, in exemplary embodiments, the control module 802 obtains a target blood glucose value for the user associated with the infusion device 702, obtains a measured (or sensed) blood glucose value from the glucose sensing arrangement 704, and performs PID control to regulate the measured value to the target value. For example, the control module 802 may include or otherwise implement a summation block that determines a difference between the target blood glucose value and the measured blood glucose value, a proportional gain block that multiplies the difference by a proportional gain coefficient, integration and gain blocks that multiply the integrated difference by an integration gain coefficient, and derivative and gain blocks that multiply the derivative of the difference by a derivative gain coefficient.

In the illustrated embodiment of FIG. 8, the data storage element 808 generally represents the hardware, circuitry and/or other components of the pump control system 720 that are configured to store the closed-loop control information for the control scheme implemented by the control module 802. The data storage element 808 may be realized as any sort of random access memory (RAM), read only memory (ROM), flash memory, registers, hard disks, removable disks, magnetic or optical mass storage, short or long term storage media, or any other non-transitory computer-readable medium. That said, in exemplary embodiments, the data storage element 808 is realized a plurality of registers associated with the control parameters for the PID control, and accordingly, the data storage element 808 may alternatively be referred to herein as the parameter registers. For example, a first register of the parameter registers 808 may store the target value for the condition being regulated, a second register of the parameter registers 808 may store the proportional gain coefficient used by the proportional gain block, a third register of the parameter registers 808 may store the integration gain coefficient, and a fourth register of the parameter registers 808 may store the derivative gain coefficient. Additional parameter registers 808 may also store or otherwise maintain insulin delivery limits for the user, along with additional user-specific PID control parameters and/or other control information referenced by the control module 802 when implementing the closed-loop PID control. In this regard, the user-specific PID control parameters may include one or more of the following: a user-specific total daily insulin value, a user-specific insulin sensitivity value, a user-specific carbohydrate ratio value, and/or other user-specific mathematical model parameter values that characterize or otherwise describe the user's insulin sensitivity and/or meal response.

Still referring to FIG. 8, the communications interface 804 generally represents the hardware, circuitry, logic, firmware and/or other components configured to support communications to/from the pump control system 800. For example, referring to FIGS. 1 and 7, the communications interface 804 may include or otherwise be coupled to one or more transceiver modules capable of supporting wireless communications between the infusion device 702 and another device (e.g., one or more of the sensing arrangements 104, 704, 706, the CCD 106, the computer 108, or the like).

Figure 9:
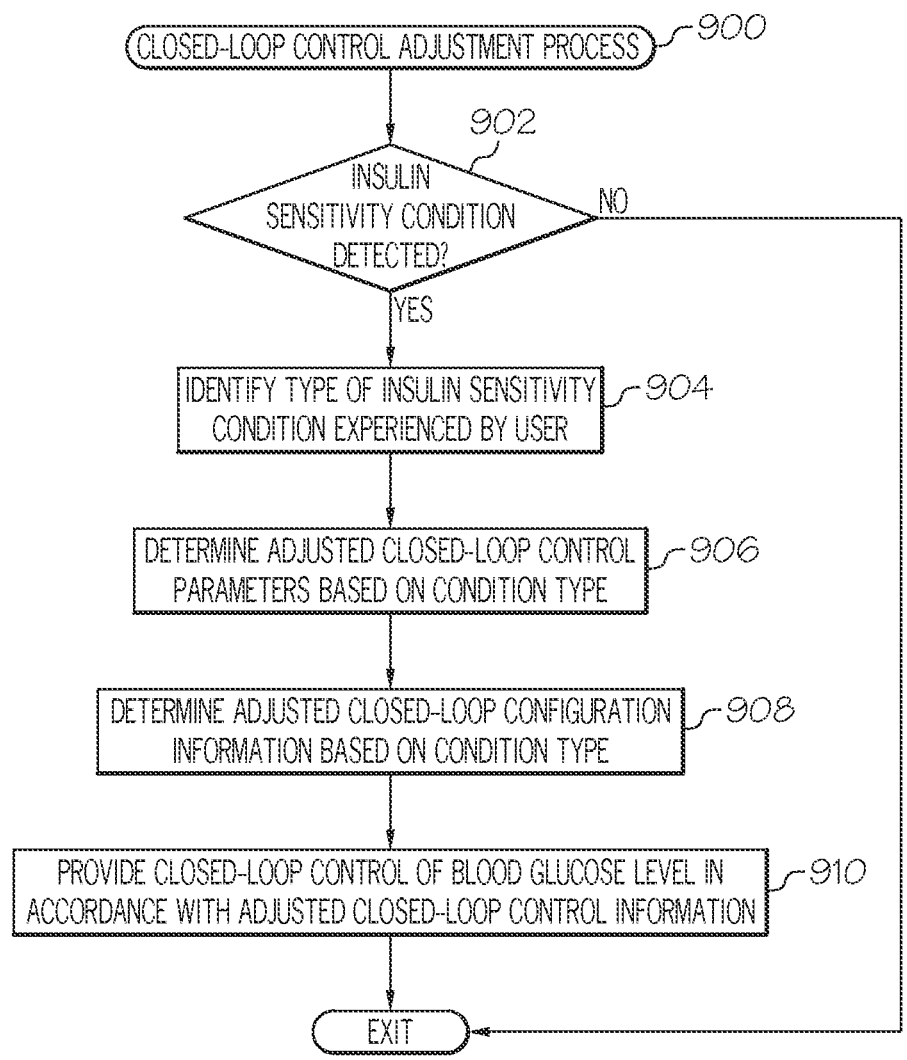
FIG. 9 is a flow diagram of an exemplary closed-loop control adjustment process.

FIG. 9 depicts an exemplary closed-loop control adjustment process 900 suitable for implementation by a control system associated with a fluid infusion device to automatically adjust control information used to generate commands for operating a motor to deliver fluid to a user in a manner that accounts for a condition in the body of the user that is likely to influence the user's response to the fluid. The various tasks performed in connection with the closed-loop control adjustment process 900 may be performed by hardware, firmware, software executed by processing circuitry, or any combination thereof. For illustrative purposes, the following description refers to elements mentioned above in connection with FIGS. 1-8. In practice, portions of the closed-loop control adjustment process 900 may be performed by different elements of an infusion system, such as, for example, the infusion device 702, one or more of the sensing arrangements 704, 706, 708, and/or the pump control system 720 in the infusion system 700 of FIG. 7. It should be appreciated that the closed-loop control adjustment process 900 may include any number of additional or alternative tasks, the tasks need not be performed in the illustrated order and/or the tasks may be performed concurrently, and/or the closed-loop control adjustment process 900 may be incorporated into a more comprehensive procedure or process having additional functionality not described in detail herein. Moreover, one or more of the tasks shown and described in the context of FIG. 9 could be omitted from a practical embodiment of the closed-loop control adjustment process 900 as long as the intended overall functionality remains intact.

In exemplary embodiments, the closed-loop control adjustment process 900 initializes or otherwise begins in response to determining to enter a closed-loop mode (e.g., closed-loop mode 530 at task 1008). Additionally, in some embodiments, the closed-loop control adjustment process 900 may also be performed at the beginning of each iteration of the closed-loop control process (e.g., at each new sampling time at task 1022) to dynamically adjust control information while the closed-loop control mode is being implemented.

In the illustrated embodiment, the closed-loop control adjustment process 900 begins by identifying, detecting, or otherwise determining whether a condition potentially affecting the user's response (or sensitivity) to the fluid being administered has occurred in the body of the user (task 902). In exemplary embodiments, the pump control system 720, 800 monitors the outputs of the sensing arrangements 706, 708 in the infusion system 700 to detect or otherwise identify a condition that is likely to influence the user's insulin response (or sensitivity), such as exercise, stress, or the like, is being or has been exhibited by the body 701. For example, the pump control system 720, 800 may periodically sample or otherwise obtain outputs from the sensing arrangements 706, 708 to obtain values for the characteristics of the body 701 measured by those sensing arrangements 706, 708, store or otherwise maintain the measured values (e.g., in memory 806), and parse or otherwise analyze the measured values to detect or otherwise identify a condition that is likely to affect the user's insulin response. In the absence of identifying an insulin sensitivity condition, the closed-loop control adjustment process 900 exits or otherwise terminates and the closed-loop mode proceeds with the pump control system 720, 800 providing closed-loop control to operate the motor 732 and regulate the user's blood glucose level based on the original control information stored in the parameter registers 808 in a similar manner as described above in the context of FIGS. 4-7.

As described in greater detail below in the context of FIG. 10, in exemplary embodiments, the pump control system 720, 800 periodically obtains the user's heart rate measurement data from the heart rate sensing arrangement 706 and analyzes the user's heart rate and heart rate variability to detect or otherwise identify whether the user's heart rate is indicative of a condition that is likely to affect the user's insulin response. In this regard, the pump control system 720, 800 may detect that the body 701 of the user is experiencing (or has experienced) exercise or stress when the user's heart rate is above a first threshold value (e.g., the heart rate detection threshold) and the user's heart rate variability is less than a second threshold value (e.g., the heart rate variability detection threshold). For example, the pump control system 720, 800 may detect that the body 701 of the user is experiencing (or has experienced) exercise or stress when the user's heart rate exceeds sixty percent of the user's maximum heart rate ($HR_{MAX}$) for at least a threshold duration of time (e.g., 20 minutes) and the user's heart rate variability decreases by at least a threshold amount (e.g., by at least twenty-five percent of the user's nominal HRV) over that duration of time.

After identifying that a condition potentially affecting the user's response has occurred, the closed-loop control adjustment process 900 continues by identifying or otherwise classifying the identified condition as a particular type of sensitivity condition from among a plurality of conditions that could potentially influence the user's response to the fluid being delivered (task 904). As described in greater detail below in the context of FIG. 10, after the pump control system 720, 800 detects that the body 701 of the user has experienced an insulin sensitivity condition based on the user's heart rate measurement data, the pump control system 720, 800 analyzes the acceleration measurement data from the acceleration sensing arrangement 708 to classify the detected condition as exercise or stress. For example, the pump control system 720, 800 may calculate or otherwise determine an activity metric associated with the user based on the acceleration measurements obtained contemporaneously to the heart rate measurement data used to identify the insulin sensitivity condition. When the magnitude of the activity metric associated with the body 701 of the user is greater than an exercise threshold value while the user's heart rate measurements are indicative of an insulin sensitivity condition, the pump control system 720, 800 classifies the detected condition as being indicative of exercise. Conversely, when the magnitude of the activity metric is less than the exercise threshold value, the pump control system 720, 800 classifies the detected condition as being indicative of stress.

In some embodiments, the pump control system 720, 800 may also detect or otherwise identify a condition that is likely to influence the user's insulin response based on user input received from the user or another individual (e.g., via the CCD 106, the computer 108, and/or a user interface associated with the infusion device 702 and/or the pump control system 720). For example, upon entering the closed-loop control mode, the user may be prompted to identify or otherwise provide input indicative of whether they have experienced a condition likely to influence his or her insulin response and identify the type of condition. The pump control system 720, 800 or another component may generate or otherwise provide a graphical user interface (GUI) on a display associated with the infusion device 702 that includes a list of conditions likely to influence insulin response with corresponding GUI elements (e.g., buttons, checkboxes, or the like) adapted to allow the user to select or otherwise indicate which (if any) of the conditions the user has experienced over a preceding duration of time (e.g., over the last 24 hours, since the most recent execution of the closed-loop mode, or the like). In this manner, the pump control system 720, 800 may receive a user input (e.g., via communications interface 804 or a user interface) that indicates or otherwise identifies the type of condition(s) likely to influence the user's insulin response that have been experienced by the user's body 701 within a preceding interval of time.

Still referring to FIG. 9, after identifying a condition likely to influence a user's response to the fluid being delivered and classifying that condition as a particular type of condition, the closed-loop control adjustment process 900 proceeds by automatically adjusting control information for the closed-loop control based on that identified type of insulin sensitivity condition, and thereafter, providing closed-loop control in accordance with the adjusted control information (tasks 906, 908, 910). In exemplary embodiments, the closed-loop control adjustment process 900 determines one or more adjusted closed-loop control parameters for implementing the closed-loop control mode that account for the anticipated change in the user's response for the identified type of condition (task 906). In this regard, the pump control system 720, 800 may adjust or otherwise modify values for one or more gain coefficients, insulin delivery limits, glucose setpoints or targets, or other control parameters utilized for the closed-loop control mode. For example, in response to detecting exercise, the pump control system 720, 800 may automatically decrease one or more of the PID gain coefficients to account for the user's anticipated increase in insulin sensitivity due to exercise, and also, decrease the maximum insulin infusion rate (e.g., upper insulin delivery limit 559) to account for the increase in the user's insulin sensitivity. In one or more embodiments, the pump control system 720, 800 stores or otherwise maintains the adjusted values for the control parameters in the parameter registers 808 (e.g., by overwriting the original values in the parameter registers 808). Alternatively, the pump control system 720, 800 may multiply the original values in the parameter registers 808 by one or more adjustment factors for the identified condition to obtain adjusted control parameter values for use in the closed-loop PID control.

In the illustrated embodiment, the closed-loop control adjustment process 900 also determines adjusted configuration information for implementing the closed-loop control on the identified type of condition (task 908). For example, in one or more embodiments, the pump control system 720, 800 calculates or otherwise determines an adjusted closed-loop control time limit for providing closed-loop control using the adjusted closed-loop control parameters. In some embodiments where the closed-loop mode may only be implemented for a specified duration of time (e.g., 8 hours), based on the identified type of condition, the pump control system 720, 800 may increase or decrease the specified duration of time for which the closed-loop mode is allowed to be implemented before triggering a fail-safe alert and/or transitioning to open-loop mode (e.g., task 1020). For example, in response to detecting stress or another condition that increases insulin resistance, the pump control system 720, 800 may reduce the duration of time for which the closed-loop mode may be provided before the closed-loop mode exits and/or a fail-safe alert (e.g., fail-safe alert 566) is generated.

In some embodiments, the pump control system 720, 800 determines an adjusted closed-loop control time limit for implementing the adjusted closed-loop control parameters before reverting to the original (or unadjusted) closed-loop control parameters for the remainder of the closed-loop mode. For example, if the closed-loop control mode is originally configured to generate the fail-safe alert 566 and/or enter the open-loop mode after eight hours, the pump control system 720, 800 determines an adjusted closed-loop control time limit based on the identified condition that is less than eight hours. Thus, after providing closed-loop PID control using the adjusted closed-loop control parameters for the adjusted closed-loop control time limit, the pump control system 720, 800 may revert to providing closed-loop PID control using the original closed-loop control parameters for the remainder of the eight hours before generating the fail-safe alert 566 and/or entering the open-loop mode.

In one or more exemplary embodiments, the pump control system 720, 800 identifies or otherwise determines a duration associated with the insulin sensitivity condition experienced by the user, and determines the adjusted closed-loop control time limit based on the duration of the condition experienced by the user. In this regard, based on timestamps associated with the heart rate and/or acceleration measurements obtained from sensing arrangements 706, 708, the pump control system 720, 800 may calculate or otherwise determine the duration of time for which the user's body 701 was exhibiting the condition. For example, the pump control system 720, 800 may calculate or otherwise determine a duration for which the user exercised based on the amount of time that the magnitude of the measured acceleration (or another activity metric) associated with the body 701 of the user is greater than the exercise threshold value. When the activity metric is less than the exercise threshold value, the pump control system 720, 800 may calculate or otherwise determine a duration for which the user was experiencing stress based on the amount of time that the user's heart rate variability was less than the heart rate variability detection threshold value while the user's heart rate was greater than the heart rate detection threshold. In one or more embodiments, the pump control system 720, 800 determines the adjusted closed-loop control time limit in a manner that correlates to the duration of the condition. In this manner, the longer that the user's body 701 experienced the identified condition, the longer the adjusted closed-loop control parameters may be utilized. For example, if the user exercises for one hour, the pump control system 720, 800 may implement the adjusted closed-loop control parameters for twice as long as when the user only exercises for thirty minutes. As described in greater detail below in the context of FIG. 10, the pump control system 720, 800 may also determine the adjusted control parameters in a manner that is based on or otherwise influenced by the duration of the insulin sensitivity condition.

In some embodiments, the pump control system 720, 800 may identify the duration of the condition based on user input received from the user or another individual in a similar manner as described above. After prompting the user to identify the type of condition(s) that the user experienced over a preceding time interval, the pump control system 720, 800 may prompt the user to input or otherwise provide an estimate of the duration of the condition(s) experienced by the user. For example, in response to receiving a user input indicating that the user exercised today, the pump control system 720, 800 may prompt the user to input or otherwise provide the duration of the exercise (e.g., by generating a text box or another GUI element on a display associated with the infusion device 702). In this manner, the pump control system 720, 800 may receive a user input (e.g., via communications interface 804 or a user interface) that indicates or otherwise identifies the duration associated with the identified type of condition(s) experienced by the user's body 701 within a preceding interval of time.

Still referring to FIG. 9, after determining the adjusted closed-loop control information based on the identified type of condition, the closed-loop control adjustment process 900 implements or otherwise provides closed-loop control in accordance with the adjusted closed-loop control information (task 910). The pump control system 720, 800 utilizes the adjusted gain coefficient(s) and/or insulin limit(s) in the parameter registers 808 (or utilizes the original gain coefficient(s) and/or insulin limit(s) in the parameter registers 808 multiplied by adjustment factor(s)) to generate delivery commands based on a measured glucose value obtained from the glucose sensing arrangement 704 to regulate the blood glucose level in the body 701 of the user, as described above in the context of FIGS. 4-8. The pump control system 720, 800 provides the adjusted closed-loop control until reaching an adjusted closed-loop control time limit or until otherwise determining the closed-loop control mode should exit (e.g., task 618). Depending on the embodiment, the pump control system 720, 800 may provide closed-loop control using the adjusted closed-loop control parameters for a duration of time that is greater than or less than the duration of time for which the pump control system 720, 800 would otherwise provide using the original closed-loop control parameters (e.g., in the absence of identifying a condition likely to influence the user's insulin response at task 902).

In some embodiments, the pump control system 720, 800 may provide closed-loop control using the adjusted closed-loop control parameters for a duration of time before reverting to the original closed-loop control parameters until generating the fail-safe alert 566 and/or entering the open-loop mode. For example, in response to detecting exercise, the pump control system 720, 800 may provide closed-loop control using decreased PID gain coefficients and an increased upper insulin limit for the adjusted closed-loop control time limit upon entering the closed-loop mode. After the adjusted closed-loop control time limit elapses, the pump control system 720, 800 may continue to provide closed-loop control using the original PID gain coefficients and original upper insulin limit until determining the closed-loop mode should terminate and entering an open-loop mode and/or generating a fail-safe alert 566.

As noted above, in some embodiments, the closed-loop control adjustment process 900 may be performed throughout implementation of the closed-loop mode (e.g., at each new sampling time) to dynamically adjust the closed-loop control information to reflect the current condition of the user's body 701. In this manner, the closed-loop control adjustment process 900 may dynamically detect a condition likely to influence the user's insulin response (or sensitivity) in real-time, and in response, dynamically adjust the control information for the closed-loop mode to reflect the current (or instantaneous) condition of the user. For example, if the pump control system 720, 800 detects that the user has begun exercising while the closed-loop mode is being implemented by the pump control system 720, 800, the pump control system 720, 800 may dynamically update or otherwise adjust one or more of the control parameters (e.g., one or more gain coefficient(s) and/or insulin limit(s)) used by the PID control so that the generated delivery commands for operating the motor 732 to account for the current state of the user's body 701. In a similar manner, in some embodiments, the closed-loop control adjustment process 900 may dynamically detect the absence of an insulin sensitivity condition, and in response, dynamically restore the control information for the closed-loop mode to the initial (or original) control information that was implemented upon initialization of the closed-loop mode. For example, if the pump control system 720, 800 detects that the user's heart rate and/or acceleration measurements have fallen below the respective thresholds indicative exercise, the pump control system 720, 800 may dynamically restore the control parameters (e.g., one or more gain coefficient(s) and/or insulin limit(s)) used by the PID control to their initial (or original) values.

Figure 10:
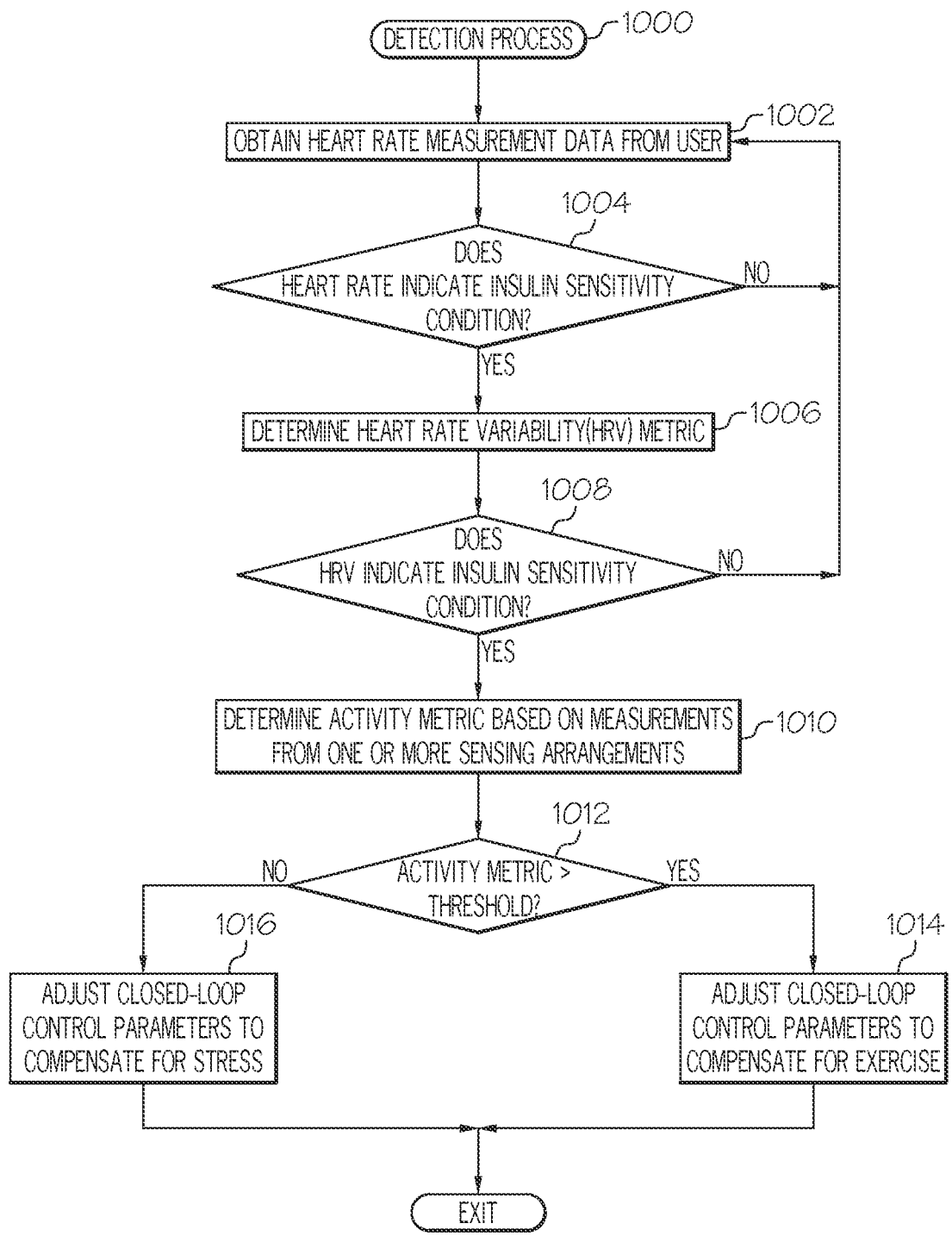
FIG. 10 is a flow diagram of an exemplary detection process suitable for use with the closed-loop control adjustment process of FIG. 9.

FIG. 10 depicts an exemplary detection process 1000 suitable for implementation to automatically detect a condition in the body of the user that is likely to influence a user's response to a fluid in conjunction with the closed-loop control adjustment process 900 (e.g., task 902) in the absence of receiving user input identifying the condition. The various tasks performed in connection with the detection process 1000 may be performed by hardware, firmware, software executed by processing circuitry, or any combination thereof. For illustrative purposes, the following description refers to elements mentioned above in connection with FIGS. 1-8. In practice, portions of the detection process 1000 may be performed by different elements of an infusion system, such as, for example, an infusion device 702, one or more sensing arrangements 704, 706, 708, and/or a pump control system 720, 800. It should be appreciated that the detection process 1000 may include any number of additional or alternative tasks, the tasks need not be performed in the illustrated order and/or the tasks may be performed concurrently, and/or the detection process 1000 may be incorporated into a more comprehensive procedure or process having additional functionality not described in detail herein. Moreover, one or more of the tasks shown and described in the context of FIG. 10 could be omitted from a practical embodiment of the detection process 1000 as long as the intended overall functionality remains intact.

In exemplary embodiments, the detection process 1000 begins by obtaining a heart rate measurement associated with the user's body and determining whether the heart rate measurement is indicative of a condition that is likely to influence the user's insulin response (tasks 1002, 1004). In this regard, the pump control system 720, 800 samples or otherwise obtains the output of the heart rate sensing arrangement 706 to obtain a measured heart rate for the body 701 of the user and determines whether the measured heart rate is greater than a threshold value indicative the user's body 701 experiencing exercise or stress. For example, the pump control system 720, 800 may detect or otherwise identify a condition likely to influence the user's insulin response when the measured heart rate value is greater than the user's nominal (or resting) heart rate value by more than a threshold percentage (e.g., more than 25% greater than the nominal heart rate) or a threshold amount (e.g., more than 2 standard deviations of the user's heart rate). For example, in one embodiment, the pump control system 720, 800 detects exercise when the measured heart rate value is greater than the user's nominal (or resting) heart rate value by more than sixty percent for more than a threshold duration of time. In an alternative embodiment, the pump control system 720, 800 detects exercise when the measured heart rate value is greater than sixty percent of the user's maximum heart rate value for more than a threshold duration of time.

In response to determining the user's heart rate is indicative of a potential insulin sensitivity condition, the detection process 1000 continues by obtaining a heart rate variability metric associated with the user's heart rate and determines whether the heart rate variability metric is also indicative of a condition that is likely to influence the user's insulin response (tasks 1006, 1008). In accordance with one or more embodiment, the pump control system 720, 800 calculates or otherwise determines the heart rate variability metric based on heart rate measurements obtained from the user's body 701. For example, the pump control system 720, 800 may buffer, store or otherwise maintain measured heart rate values for the user that were obtained over a preceding time interval (e.g., the preceding 5 minutes) and calculate the user's heart rate variability by performing spectral analysis on the measured heart rate values. In one embodiment, the pump control system 720, 800 calculates the user's heart rate variability as the standard deviation of the user's measured heart rate values over a preceding one minute time interval. In yet other embodiments, the heart rate sensing arrangement 706 may determine the heart rate variability and provide the user's heart rate variability to the pump control system 720, 800 as an output from the heart rate sensing arrangement 706.

After obtaining the heart rate variability metric, the pump control system 720, 800 compares the heart rate variability metric to a threshold value indicative of an insulin sensitivity condition. In this regard, a user's heart rate variability typically decreases during both exercise and stress relative to the user's nominal heart rate variability in the absence of an insulin sensitivity condition. Accordingly, in the illustrated embodiment, the pump control system 720, 800 detects or otherwise identifies the heart rate variability metric as being indicative of exercise or stress when the heart rate variability metric decreases by at least a threshold percentage of the user's nominal heart rate variability (e.g., a 25% decrease in the user's HRV).

In response to determining both the heart rate and the heart rate variability are indicative of an insulin sensitivity condition, the detection process 1000 continues by obtaining an activity metric associated with the user and determining whether the activity metric is indicative of the detected condition being stress or exercise (tasks 1010, 1012). In this regard, the pump control system 720, 800 classifies or otherwise identifies the type for the detected condition (e.g., task 904) as being exercise when the activity metric is greater than an exercise threshold value, and conversely, the pump control system 720, 800 classifies or otherwise identifies the type for the detected condition as being stress when the activity metric is less than the exercise threshold value. In accordance with one or more embodiments, the pump control system 720, 800 calculates or otherwise determines the activity metric based on acceleration measurements associated with the user's body 701 that are or were obtained from the acceleration sensing arrangement 708 contemporaneously to the heart rate measurement values.

In a similar manner as described above, the pump control system 720, 800 may buffer, store or otherwise maintain the current and previous measured acceleration values that were obtained over a preceding time interval and calculate the user's activity metric based on those measured acceleration values. For example, the pump control system 720, 800 may calculate or otherwise determine an average magnitude of acceleration for the user's body 701 over the preceding time interval (e.g., the preceding 5 minutes) contemporaneous to the heart rate measurements used for determining the heart rate variability metric. When the acceleration is greater than the exercise threshold value over the preceding time interval where the heart rate measurements indicate stress or exercise, the pump control system 720, 800 classifies or otherwise identifies the detected condition as being exercise. Conversely, when the acceleration is less than the exercise threshold value over the preceding time interval where the heart rate measurements indicate stress or exercise (e.g., when the user's HRV decreases by at least 25% relative to the user's nominal HRV), the pump control system 720, 800 classifies or otherwise identifies the detected condition as being stress.

In response to detecting or otherwise identifying exercise, the detection process 1000 continues by adjusting the closed-loop control information (e.g., tasks 906, 908) to compensate for exercise (task 1014). In this regard, an increase in physical activity amplifies glucose uptake by the working tissues. For non-diabetic persons, glucose homeostasis is maintained by lowering endogenous insulin secretion and increasing hepatic glucose production due to elevated glucagon and catecholamine levels. For type 1 diabetic mellitus (T1DM) patients, the above-mentioned hormonal adaptation during elevated physical activity is greatly diminished. As a result, presence of high levels of exogenous insulin in the circulation may prevent mobilization of glucose during exercise causing hypoglycemia. Conversely, too little insulin in the circulation may result in excessive release of counter-insulin hormones during exercise which may cause hyperglycemia.

Based on the intensity and duration of exercise detected by the pump control system 720, 800, the amount of energy expenditure (AEE) during exercise can be determined by the following equation: $AEE = MET \times RMR \times BW \times D$, where RMR is the resting metabolic rate in kilocalories (kcal) per kilogram per hour (which is a function of the body weight, age, height, and gender), MET is a multiplier (scaling factor) for the metabolic equivalent task representing the intensity of the exercise, BW is body weight in kilograms, and D is the duration of exercise in hours. During a resting period, $MET=1.0$, and resting energy expenditure can be determined by the following equation: $AEE_R = RMR \times BW \times D$. Therefore, the relative AEE ($\overline{AEE}$) can be obtained as $\overline{AEE} = AEE - AEE_R$. Glycemic level changes for T1DM patients due to exercise can be written as $\Delta G = G_F - G_0$, where $G_F$ is the glucose concentration (mg/dL) after exercise and $G_0$ is the glucose concentration (mg/dL) before exercise.

By way of example, the relationship between the change in glucose level ($\Delta G$) and exercise can be mathematically represented by the following equation: $\Delta G = f_{I_E} \times \overline{AEE}(IOB_1 - IOB)$, where $IOB_1$ is the ideal insulin-on-board (U) at elevated activity level, IOB is the actual insulin-on-board (U), and $f_{I_E}$ is the activity insulin equivalent factor. If IOB is equal to $IOB_1$ then the net AG will be equal to zero, indicating an ideal plasma insulin level during exercise thereby causing a perfect glucose homeostasis (no change) which is usually the case for non-diabetics. On the other hand, $IOB < IOB_1$ will cause a positive AG (elevated glucose level in post-exercise period), and $IOB > IOB_1$ will cause a negative AG (reduced glucose level in post-exercise period) which is the most predominant scenario for T1DM patients. The drop in glucose concentration due to physical activity (e.g., when $\Delta G < 0$) can be converted to an equivalent insulin amount ($I_{EQ}$) in units (U) by using the patient's insulin sensitivity factor (SI in mg/dL/U) as follows:

$$I_{EQ} = \left| \frac{\Delta G}{SI} \right|.$$

In accordance with one or more embodiments, in response to detecting exercise, an adjusted reduced proportional gain coefficient ($K_P^*$) may be calculated by estimating the amount of energy expenditure, calculating the change in glycemic level, and determining the equivalent insulin amount before using the equation:

$$K_P^* = \frac{60}{90} \times \frac{DIR - I_{EQ}}{1500},$$

where DIR is the daily insulin requirement in units (U).

In accordance with one or more embodiments, in response to detecting exercise, an adjusted increased glucose target (or setpoint) for the closed-loop control is calculated when $\Delta G < 0$ using the equation: $G_T^* = G_T + k \times |\Delta G|$, where $G_T$ is the nominal glucose target, $G_T^*$ is the adjusted glucose target, and k is a scaling factor between zero and one. In this regard, the scaling factor influences the amount or rate of adjustment for the glucose target, where increasing the value of k increases the amount or rate of adjustment and decreasing the value of k decreases the amount or rate of adjustment. In some embodiments, the value of k may be fixed or predetermined when the infusion device 700 is deployed. In other embodiments, the value of k may be set or otherwise adjusted by a user, such as a doctor or the patient. In yet other embodiments, the value of k may be dynamically determined based on the user's historical response to exercise that is observed over the lifetime of the infusion device 700. In this regard, the value of the scaling factor may be dynamically adjusted to account for changes in the user's observed response to exercise as the user ages, experiences lifestyle changes, or the like.

In exemplary embodiments, in response to detecting exercise, an adjusted upper insulin delivery limit is also calculated to compensate for changes to the user's insulin response (or sensitivity). The delivery limit is calculated based on the patient's basal rate, fasting blood glucose, and insulin sensitivity. Examination of the post night fasting blood glucose (FBG) levels allows an estimate of a single FBG value ($FBG_0$) that is a function of the overnight basal insulin ($I_{basal,0}$). Having estimated $FBG_0$, its corresponding $I_{basal,0}$, and KI, an estimate of the insulin maximum delivery rate ($U_{max}$) can be made. Thus, if the delivery of insulin were to occur at the $U_{max}$, this would result in a fasting blood glucose level defined by $BG_{LBL}$, which is the lower buffer limit. $U_{max}$ is calculated by the following equation:

$$U_{max} = I_{basal,0} + \frac{BG_{LBL} - FBG_0}{KI}, \text{ where } KI = -3 \times \frac{1800}{DIR}.$$

In accordance with one embodiment, in response to detecting exercise, when $\Delta G < 0$, an adjusted estimated fasting blood glucose value is calculated using the equation $FBG_0^* = FBG_0 + \Delta G$ and an adjusted upper insulin limit ($U_{max}^*$) is calculated based on the adjusted estimated fasting blood glucose value using the equation:

$$U_{max}^* = I_{basal,0} + \frac{BG_{LBL} - FBG_0^*}{KI}.$$

In an alternative embodiment, in response to detecting exercise, an adjusted daily insulin requirement is calculated using equation $DIR^* = DIR - I_{EQ}$, an adjusted and the adjusted upper insulin limit is calculated using the equation $$U_{max}^* = I_{basal,0} + \frac{BG_{LBL} - FBG_0}{KI^*}, \text{ where } KI^* = -3 \times \frac{1800}{DIR^*}.$$

In accordance with yet another embodiment, in response to detecting exercise, the adjusted upper insulin delivery limit is chosen to be equal to the overnight basal insulin ($I_{basal,0}$).

Exercise can have has a prolonged effect on the insulin sensitivity, and therefore, in exemplary embodiments, in addition to adjusting the control parameters (e.g., $K_P^*$, $G_T^*$, $U_{max}^*$), the pump control system 720, 800 calculates or otherwise determines an adjusted closed-loop control time limit (e.g., task 908) as a function of the duration of the exercise and the intensity. In this regard, the adjusted closed-loop control time limit ensures that the adjusted closed-loop control parameters are implemented for a sufficiently long duration of time to account for the anticipated prolonged effect of the exercise on the user's insulin response based on the duration and intensity of the exercise.

Still referring to FIG. 10, in response to detecting or otherwise identifying stress, the detection process 1000 continues by adjusting the closed-loop control information (e.g., tasks 906, 908) to compensate for stress (task 1016). Under stress the body behaves as if it is under attack, and it prepares itself to take action, which is commonly known as the fight-or-flight response. Under such a condition, the hormone levels are significantly elevated. The net effect is to make a lot of stored energy (e.g., glucose and fat) available to the cells in order to take necessary action. For T1DM patients, the stress induced elevated levels of glucose cannot be metabolized properly due to lack of insulin. As a result, majority of T1DM patients experience stress induced chronic hyperglycemia. However, studies have also reported that some T1DM patients might even undergo hypoglycemia due to stress.

In accordance with one embodiment, the effect of stress on blood glucose concentration is estimated using the equation: $\Delta G = f_{STRESS} \times S_I$, where $f_{STRESS}$ is a stress scaling factor, $S_I$ is an estimate of the stress intensity, and $\Delta G$ is the change in glucose level before and after stress. The stress scaling factor ($f_{STRESS}$) maps the stress intensity to the user's change in glucose level. In exemplary embodiments, the stress scaling factor is patient-specific and will be positive for patients that experience hyperglycemia due to stress and negative for patients that experience hypoglycemia due to stress. The pump control system 720, 800 calculates or otherwise determines the stress intensity ($S_I$) based on the user's heart rate variability. In this regard, the stress intensity ($S_I$) may correspond to the amount of the decrease in the user's heart rate variability (e.g., a greater decrease corresponds to a greater stress intensity) and/or the duration of time over which the user's heart rate variability decreased (e.g., a greater duration of decreased heart rate variability corresponds to a greater stress intensity).

In a similar manner as described above in the context of exercise, after an estimated change in glucose level is determined, an equivalent insulin amount ($I_{EQ}$) can be determined based on the estimated change in glucose level, and an adjusted proportional gain coefficient is calculated as $$K_P^* = \frac{60}{90} \times \frac{DIR + I_{EQ}}{1500}, \text{ where } I_{EQ} = \frac{\Delta G}{SI}.$$

In this regard, when $\Delta G > 0$, the adjusted proportional gain coefficient is increased relative to the initial (or unadjusted original) proportional gain coefficient. An adjusted decreased glucose target (or setpoint) for the closed-loop control may also be calculated when $\Delta G > 0$ using the equation: $G_T^* = G_T - k \times \Delta G$. Additionally, an adjusted upper insulin limit ($U_{max}^*$) is calculated based on the adjusted estimated fasting blood glucose value using the equation:

$$U_{max}^* = I_{basal,0} + \frac{BG_{LBL} - FBG_0^*}{KI}, \text{ where } FBG_0^* = FBG_0 + \Delta G.$$

In this regard, when $\Delta G > 0$, the adjusted upper insulin limit is increased relative to the initial (or unadjusted original) upper insulin limit (e.g., $U_{max}^* > U_{max}$). In an alternative embodiment, in response to detecting stress, an adjusted daily insulin requirement is calculated using an adjusted daily insulin requirement as described above $$\left(\text{e.g., } DIR^* = DIR + I_{EQ}, \text{ where } I_{EQ} = \frac{\Delta G}{SI}\right).$$

In one or more embodiments, in addition to adjusting the control parameters, the pump control system 720, 800 calculates or otherwise determines an adjusted closed-loop control time limit (e.g., task 908) as a function of the duration of the stress and the stress intensity to account for the anticipated duration for the stress's impact on the user's insulin response.

To briefly summarize, the subject matter described herein allows for an insulin sensitivity condition, such as exercise or stress, to be automatically detected and classified as a particular type of insulin sensitivity condition based on characteristics associated with the user's body (e.g., heart rate measurements, acceleration measurements, or the like). In response to detecting and classifying an insulin sensitivity condition, closed-loop control information used when providing closed-loop control of the user's blood glucose level is automatically adjusted based on the identified insulin sensitivity condition to account for the anticipated changes in the user's insulin response. One or more PID gain coefficients, insulin delivery limits, setpoints or targets, and/or other control parameters used to generate insulin delivery commands may be automatically adjusted to compensate for the changes in the user's insulin sensitivity. Additionally, configuration information (e.g., time limits or the like) utilized in providing closed-loop control may also be automatically adjusted. Thus, the user's blood glucose level may be more effectively managed using closed-loop control in a manner that does not require a user or another individual (e.g., the user's doctor, nurse, caretaker, or the like) to manually adjust the control information on a daily basis to account for the user's daily activities. Additionally, in some embodiments, the closed-loop control information may be dynamically adjusted in real-time to account for the current state of the user when the user begins experiencing an insulin sensitivity condition while closed-loop control mode is being provided.

For the sake of brevity, conventional techniques related to glucose sensing and/or monitoring, sensor calibration and/or compensation, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion system comprising:
  a motor operable to deliver fluid to a user, delivery of the fluid influencing a first condition of the user;
  a sensing arrangement to obtain a measured value indicative of the first condition of the user;
  a heart rate sensing arrangement to obtain heart rate measurement data for the user; and
  a control system coupled to the motor, the heart rate sensing arrangement, and the sensing arrangement to:
    determine a heart rate variability metric for the user based on a spectral analysis of the heart rate measurement data;
    detect a second condition of the user that is likely to influence a response to the fluid in a body of the user based on the heart rate measurement data when a measured heart rate for the user is greater than a first threshold value and the heart rate variability metric is less than a second threshold value;
    classify the second condition as exercise; and
    after classifying the second condition as exercise:
      adjust control information for operating the motor, resulting in adjusted control information; and
      operate the motor to deliver the fluid to the user based at least in part on the adjusted control information and a difference between a target value for the first condition of the user and the measured value, wherein:
      the adjusted control information comprises a decreased gain coefficient; and
      the control system determines the decreased gain coefficient by estimating an amount of energy expenditure during the exercise, calculating a change in glycemic level for the user based on the amount of energy expenditure, determining an equivalent insulin amount based on the change in glycemic level, and determining an adjusted proportional gain coefficient based on a first difference between a daily insulin requirement for the user and the equivalent insulin amount.

2. The infusion system of claim 1, wherein the control system operates the motor to deliver the fluid to the user based at least in part on the adjusted control information by determining a delivery command using the decreased gain coefficient and operating the motor in accordance with the delivery command.

3. The infusion system of claim 2, wherein the adjusted control information further comprises an increased delivery limit.

4. The infusion system of claim 1, further comprising an acceleration sensing arrangement to obtain acceleration measurement data for the user, wherein the control system is coupled to the acceleration sensing arrangement to:
  determine an activity metric for the user based on the acceleration measurement data;
  classify the second condition as exercise when the activity metric is greater than an exercise threshold value; and
  classify the second condition as stress when the activity metric is less than the exercise threshold value.

5. The infusion system of claim 4, wherein in response to classifying the second condition as exercise, the control system is configured to:
  adjust the control information by decreasing a gain coefficient value; and
  operate the motor by:
    applying the gain coefficient value to the difference between the target value and the measured value to obtain a delivery command; and
    operating the motor in accordance with the delivery command.

6. The infusion system of claim 4, wherein in response to classifying the second condition as stress, the control system is configured to:
  adjust the control information by increasing a gain coefficient value; and
  operate the motor by:
    applying the gain coefficient value to the difference between the target value and the measured value to obtain a delivery command; and
    operating the motor in accordance with the delivery command.

7. The infusion system of claim 1, wherein the control system operates the motor to deliver the fluid to the user based at least in part on the adjusted control information by:
  determining a delivery command by applying the adjusted proportional gain coefficient to the difference between the target value for the first condition of the user and the measured value; and
  operating the motor in accordance with the delivery command.

8. The infusion system of claim 1, wherein the control system operates the motor by applying the adjusted control information to the difference to produce a delivery command and operating the motor in accordance with the delivery command to deliver the fluid to the user.

9. The infusion system of claim 1, wherein:
the fluid comprises insulin; and
the second condition comprises an insulin sensitivity condition.

10. An infusion system comprising:
a motor operable to deliver fluid to a user, delivery of the fluid influencing a first condition of the user;
a sensing arrangement to obtain a measured value indicative of the first condition of the user;
a heart rate sensing arrangement to obtain heart rate measurement data for the user; and
a control system coupled to the motor, the heart rate sensing arrangement, and the sensing arrangement to:
  determine a heart rate variability metric for the user based on a spectral analysis of the heart rate measurement data;
  detect a second condition of the user that is likely to influence a response to the fluid in a body of the user based on the heart rate measurement data when a measured heart rate for the user is greater than a first threshold value and the heart rate variability metric is less than a second threshold value;
  classify the second condition as stress; and
  after classifying the second condition as stress:
    adjust control information for operating the motor, resulting in adjusted control information; and
    operate the motor to deliver the fluid to the user based at least in part on the adjusted control information and a difference between a target value for the first condition of the user and the measured value, wherein:
      the adjusted control information comprises an increased gain coefficient; and
      the control system determines the increased gain coefficient by estimating a change in glycemic level for the user based at least in part on an intensity of the stress, determining an equivalent insulin amount based on the change in glycemic level, and determining an adjusted proportional gain coefficient based on a first difference between a daily insulin requirement for the user and the equivalent insulin amount.

11. The infusion system of claim 10, wherein the control system operates the motor to deliver the fluid to the user based at least in part on the adjusted control information by determining a delivery command using the increased gain coefficient and operating the motor in accordance with the delivery command.

12. The infusion system of claim 11, wherein the adjusted control information further comprises a decreased delivery limit.

13. The infusion system of claim 10, wherein the control system operates the motor to deliver the fluid to the user based at least in part on the adjusted control information by:
determining a delivery command by applying the adjusted proportional gain coefficient to the difference between the target value for the first condition of the user and the measured value; and
operating the motor in accordance with the delivery command.

14. An infusion system comprising:
a motor operable to deliver fluid to a user, delivery of the fluid influencing a first condition of the user;
a sensing arrangement to obtain a measured value indicative of the first condition of the user; and
a control system coupled to the motor and the sensing arrangement to identify a second condition of the user that is likely to influence a response to the fluid in a body of the user, classify the second condition as exercise, and after classifying the second condition as exercise:
  estimate an amount of energy expenditure during the exercise;
  calculate a change in glycemic level for the user based on the amount of energy expenditure;
  determine an equivalent insulin amount based on the change in glycemic level;
  determine a decreased proportional gain coefficient based on a first difference between a daily insulin requirement for the user and the equivalent insulin amount; and
  operate the motor to deliver the fluid to the user based at least in part on the decreased proportional gain coefficient and a difference between a target value for the first condition of the user and the measured value.

15. An infusion system comprising:
a motor operable to deliver fluid to a user, delivery of the fluid influencing a first condition of the user;
a sensing arrangement to obtain a measured value indicative of the first condition of the user; and
a control system coupled to the motor and the sensing arrangement to identify a second condition of the user that is likely to influence a response to the fluid in a body of the user, classify the second condition as stress, and after classifying the second condition as stress:
  estimate a change in glycemic level for the user based at least in part on an intensity of the stress;
  determine an equivalent insulin amount based on the change in glycemic level;
  determine an increased proportional gain coefficient based on a first difference between a daily insulin requirement for the user and the equivalent insulin amount; and
  operate the motor to deliver the fluid to the user based at least in part on the increased proportional gain coefficient and a difference between a target value for the first condition of the user and the measured value.

* * * * *